(12) United States Patent
Dantus et al.

(10) Patent No.: US 10,598,682 B2
(45) Date of Patent: Mar. 24, 2020

(54) LASER SYSTEM FOR MEASURING FLUID DYNAMICS

(71) Applicant: Board of Trustees of Michigan State University, East Lansing, MI (US)

(72) Inventors: Marcos Dantus, Okemos, MI (US); Manoochehr M. Koochesfahani, Okemos, MI (US); Shahram Pouya, East Lansing, MI (US); Anton G. Ryabtsev, East Lansing, MI (US); Alireza Safaripour Tabalvandani, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 241 days.

(21) Appl. No.: 15/429,739

(22) Filed: Feb. 10, 2017

(65) Prior Publication Data

US 2018/0267072 A1 Sep. 20, 2018

Related U.S. Application Data

(60) Provisional application No. 62/294,699, filed on Feb. 12, 2016.

(51) Int. Cl.
*G01N 21/64* (2006.01)
*G01P 5/00* (2006.01)
*G01P 5/26* (2006.01)

(52) U.S. Cl.
CPC .......... *G01P 5/001* (2013.01); *G01N 21/645* (2013.01); *G01P 5/26* (2013.01); *G01N 2201/06113* (2013.01)

(58) Field of Classification Search
CPC ....... G01N 21/645; G01N 2201/06113; G01N 15/1434; G01N 15/1425; G01N 15/147
See application file for complete search history.

(56) References Cited

U.S. PATENT DOCUMENTS

| 3,952,577 A | * | 4/1976 | Hayes | G01F 1/36 73/54.04 |
| 4,223,226 A | | 9/1980 | Quick et al. | |
| 4,385,830 A | * | 5/1983 | Webb | G01P 5/01 356/28 |
| 4,440,030 A | * | 4/1984 | Pounder | G01F 1/06 73/861.87 |

(Continued)

OTHER PUBLICATIONS

Belnnonte et al.,,A Measure of Flow Vorticity with Helical Beams of Light, Jul. 2015, Optical Society of American, vol. 2, No. 11, Optica, pp. 1002-1005.*

(Continued)

*Primary Examiner* — David P Porta
*Assistant Examiner* — Djura Malevic
(74) *Attorney, Agent, or Firm* — Harness, Dickey & Pierce, PLC

(57) ABSTRACT

The superposition of Laguerre-Gaussian guided into and scattered by a particle in a rotated fluid allows the detection of the rotational of the fluid. The presented system allows for virtually real-time determination of vorticity characterization in a fluid. The system allows the direct measurements of fluid flow vorticity using a spatially shaped beam with a superposition of Laguerre-Gaussian modes that reports on the rotational Doppler shift from microparticles intersecting the beam focus.

38 Claims, 17 Drawing Sheets

(56) References Cited

U.S. PATENT DOCUMENTS

| | | | | |
|---|---|---|---|---|
| 4,664,513 | A * | 5/1987 | Webb | G01P 5/26 356/28 |
| 5,359,418 | A * | 10/1994 | Zaleski | G01B 11/08 250/559.24 |
| 6,134,001 | A | 10/2000 | Black | |
| 6,204,499 | B1 * | 3/2001 | Schaefer | G01D 5/30 250/227.14 |
| 6,762,827 | B2 * | 7/2004 | Aroussi | A61B 5/027 356/28 |
| 6,874,480 | B1 * | 4/2005 | Ismailov | F02D 41/40 123/494 |
| 8,743,351 | B2 | 6/2014 | Christian et al. | |
| 2002/0014224 | A1 * | 2/2002 | Ismailov | F02D 41/40 123/494 |
| 2003/0099264 | A1 | 5/2003 | Dantus et al. | |
| 2003/0133096 | A1 * | 7/2003 | Aroussi | A61B 5/027 356/28 |
| 2004/0089804 | A1 | 5/2004 | Dantus et al. | |
| 2004/0233944 | A1 | 11/2004 | Dantus et al. | |
| 2005/0021243 | A1 | 1/2005 | Dantus et al. | |
| 2005/0232317 | A1 | 10/2005 | Dantus et al. | |
| 2006/0056468 | A1 | 3/2006 | Dantus et al. | |
| 2006/0146910 | A1 | 7/2006 | Koochesfahani et al. | |
| 2006/0187974 | A1 | 8/2006 | Dantus | |
| 2006/0274313 | A1 | 12/2006 | Gilbert et al. | |
| 2008/0170218 | A1 | 7/2008 | Dantus et al. | |
| 2009/0122819 | A1 | 5/2009 | Dantus et al. | |
| 2009/0188901 | A1 | 7/2009 | Dantus | |
| 2009/0207869 | A1 | 8/2009 | Dantus et al. | |
| 2009/0216299 | A1 | 8/2009 | Dantus | |
| 2009/0238222 | A1 | 9/2009 | Dantus et al. | |
| 2009/0256071 | A1 | 10/2009 | Dantus et al. | |
| 2009/0257464 | A1 | 10/2009 | Dantus et al. | |
| 2009/0296744 | A1 | 12/2009 | Dantus et al. | |
| 2010/0123075 | A1 | 5/2010 | Dantus et al. | |
| 2010/0187208 | A1 | 7/2010 | Dantus et al. | |
| 2011/0171320 | A1 | 7/2011 | Dantus | |
| 2011/0211600 | A1 | 9/2011 | Dantus et al. | |
| 2012/0076504 | A1 | 3/2012 | Dantus et al. | |
| 2012/0147911 | A1 | 6/2012 | Dantus et al. | |
| 2014/0058367 | A1 | 2/2014 | Dantus | |
| 2015/0157209 | A1 | 6/2015 | Dantus | |
| 2016/0137271 | A1 * | 5/2016 | MacCready | B63B 22/18 114/338 |
| 2016/0169806 | A1 | 6/2016 | Dantus et al. | |

OTHER PUBLICATIONS

Antonia, R.A., et. al.; "Conditionally Sampled Measurements in a Heated Turbulent Jet," J. Fluid Mech., vol. 72, 1975, pp. 455-480.
Ballew, R.M., et al.; "An Error Analysis of the Rapid Lifetime Determination Method for the Evaluation of Single Exponential Decay," Anal. Chem., vol. 61, 1989, pp. 30-33.
Bohl, D.G., et al.; "Development of Stereoscopic Molecular Tagging Velocimetry," Exp. Fluids, vol. 30, No. 2, 2001, pp. 302-308.
Bohl, D.G., et al; "Molecular Tagging Velocimetry Measurements of Axial Flow in a Concentrated Vortex Core," Physics of Fluids, vol. 16, No. 11, Nov. 2004, pp. 4185-4191.
Bohl, D.G., et al.; "MTV Measurements of the Vortical Field in the Wake of an Airfoil Oscillating at High Reduced Frequency," J. Field Mech., vol. 620, 2009, pp. 63-88.
Brewster, R.E., et al.; "Optical Thermometer Based on the Stability of a Phosphorescent 6-Bromo-2-Naphthal/α-Cyclodextrin2 Ternary Complex," Chem. Commun., 2001, pp. 1134-1135.
Chevray, R., et al.; "Intermittency and Preferential Transport of Heat in a Round Jet," J. Fluid Mech., vol. 88, 1978, pp. 133-160.
Cohn, R. K., et al.; "The Accuracy of Remapping Irregularity Spaced Velocity Data Onto a Regular Grid and the Computation of Vorticity," Experiments in Fluids (Suppl.), 2000, pp. 561-569.
Cohn, R.K., et al.; "Vorticity Field Evolution in a Forced Wake," Proceedings of the 1st International Symposium on Turbulence and Shear Flow Phenomena, Santa Barbara, CA, Eds. Banerjee, S. and Eaton, J.K., Sep. 12-15, 1999, pp. 901-906.
Coppeta, J., et al.; "Dual Emission Laser Induced Fluorescence for Direct Planar Scalar Behavior Measurements," Experiments in Fluids, vol. 25, No. 1, 1998, pp. 1-15.
Dabiri, D., et al.; "Digital Particle Image Thermometry: The Method and Implementation," Experiments in Fluids, vol. 11, 1991, pp. 77-86.
Dibble, R.W., et al.; Conserved Scalar Fluxes Measurement in a Turbulent Non-Premixed Flame by Combined Laser Doppler Velocimetry and Laser Raman Scattering, Combustion and Flame, vol. 55, 1984, pp. 307-321.
Falco, R.E., et al.; "Quantitative Multipoint Measurements and Visualization of Dense Solid-Liquid Flows Using Laser Induced Photochemical Anemometry (LIPA)," in Particulate Two-Phase Flow, Ed. M.C. Rocco; Butterworth-Heinemann, 1993, pp. 59-126.
Gendrich, C.P., et al.; "A Spatial Correlation Technique for Estimating Velocity Fields Using Molecular Tagging Velocimetry (MTV)," Experiments in Fluids, vol. 22, No. 1, 1996, pp. 67-77.
Gendrich, C.P., et al.; "Molecular Tagging Velocimetry and Other Novel Application of a New Phosphorescent Supramolecule," Experiments in Fluids, vol. 23, 1997, pp. 361-372.
Grissino, A.S., et al.; "Combined Dual Emission LIF and PIV to Resolve Temperature and Velocity," Proceedings of the 3rd International Workshop on Particle Image Velocimetry, Sep. 16-18, 1999, Santa Barbara, CA, U.S.A., pp. 591-597.
Hartmann, W.K., et al.; "Substrate Induced Phosphorescence From Cyclodextrin-Lumophore Host-Guest Complex," Inorganica Chimica Acta., vol. 243, 1996, pp. 239-248.
Hishida, K., et al.; "Combined Planar Laser-Induced Fluorescence—Particle Image Velocimetry Technique for Velocity and Temperature Fields," Experiments in Fluids, vol. 29, 2000, pp. s129-s140.
Hu, H., et al.; "A Novel Technique for Quantitative Temperature Mapping in Liquid by Measuring the Lifetime of Laser Induced Phosphorescence," Journal of Visualization, vol. 6, No. 2, 2003, pp. 143-153.
Hu, H., et al.; (submitted 2005) "Molecular Tagging Thermometry With Adjustable Temperature Sensitivity," Experiments in Fluids, vol. 40, (published 2006), pp. 753-763.
Hu, H., et al.; "Thermal Effects on the Wake of a Heated Circular Cylinder Operating in Mixed Convection Regime," J. Fluid Mech., vol. 685, 2011, pp. 235-270.
Koochesfahani, M.M., et al.; "Molecular Tagging Diagnostics for the Study of Kinematics and Mixing in Liquid Phase Flows," Proceedings of the Eighth International Symposium on Applications of Laser Techniques to Fluids Mechanics, Jul. 8-11, 1996, Lisbon, Portugal, vol. I, pp. 1.2.1-1.2.12; Also in Developments in Laser Techniques and Fluid Mechanics, Chapter 2, section 1, p. 125, Eds. Adrian. Durao, Durst, Maeda, and Whitelaw; Springer-Verlag, Berlin, 1997.
Koochesfahani, M.M.; "Molecular Tagging Velocimetry (MTV): Progress and Applications," AIAA Paper No. AIAA-99-3786; 1999.
Koochesfahani, M., et al.; "Simultaneous Whole-Field Measurements of Velocity and Concentration Fields Using a Combination of MTV and LIF," Meas. Sci. Technol., 11, 2000, pp. 1289-1300.
Kotsovinos, N.E.; "Plane Turbulent Buoyant Jets," J. Fluid Mech., vol. 81, 1997, pp. 45-62.
Lavielle, P., et al.; "Evaporating and Combusting Droplet Temperature Measurements Using Two-Color Laser-Induced Fluorescence," Experiments in Fluids, vol. 31, No. 1, 2001, pp. 45-55.
Lemoine, L., et al; "Simultaneous Temperature and 2D Velocity Measurements in a Turbulent Heated Jet Using Combined Laser-Induced Fluorescence and LDA," Experiments in Fluids, vol. 26., 1999, pp. 315-323.
Lempert, W.R., et al.; "Molecular Tagging Velocimetry and Thermometry." Flow Visualization Techniques and Examples, Chapter 4, Editors: A.J. Smits and T.T. Lim, Imperial College Press, Second Edition, 2011, pp. 79-105.
Lempert, W.R., et al.; "Molecular Tagging Velocimetry," 25 pgs, appearing in Visualization—Techniques and Examples, Ed. A.J. Smits and T.T. Lim (London: Imperial College Press, London), 2000, pp. 73-92.

(56) References Cited

OTHER PUBLICATIONS

Mortellaro, M.A. et al.; "A Turn-on for Optical Sensing," Chemical Technology, vol. 26, 1996, pp. 17-23.

Olsen, D.A., et al.; "An Investigation of the Effect of Freestream Turbulence on the Laminar Separation Bubble on an SD7003 Airfoil," 49th AIAA Aerospace Sciences Meeting including the New Horizons Forum and Aerospace Exposition, Orlando, Florida, Jan. 4-7, 2011, pp. 1-9.

Park, H.G., et al.; "Digital Particle Image Velocimetry/ Thermometry and Application to the Wake of a Heated Circular Cylinder," Experiments in Fluids, vol. 30, 2001, pp. 327-338.

Ponce, A., et al.; "Intense Phosphorescence Triggered by Alcohols Upon Formation of a Cyclodextrin Ternary Complex," Journal of Physical Chemistry, vol. 97, 1993, pp. 11137-11142.

Pouya, S., et al.; "Experimental Evidence of Diffusion-Induced Bias in Near-Wall Velocimetry Using Quantum Dot Measurements," Exp. Fluids, 44, 2008, pp. 1035-1038.

Pouya, S., et al.; "Multi-Photon Molecular Tagging Velocimetry With Femtosecond Excitation (FemtoMTV)," Exp. Fluids, 55: 1791, Jul. 17, 2014, five pages.

Sakakibara, J., et al.; "Vortex Structure and Heat Transfer in the Stagnation Region of an Impinging Plane Jet," Int. J. Heat and Mass Transfer, vol. 40, 1997, pp. 3163-3176.

Sakakibara, J., et al; "Whole Field Measurement of Temperature in Water Using Two-Color Laser Induced Fluorescence," Experiments in Fluids, vol. 26, No. 1, 1999, pp. 7-15.

Ryabtsev, A, et al.; "Fluid Flow Vorticity Measurement Using Laser Beams With Orbital Angular Momentum," Optics Express, vol. 24, No. 11, May 30, 2016, pp. 11762-11767.

Ryabtsev, A., et al.; "Vortices in the Wake of a Femtosecond Laser Filament," Optics Express, vol. 22, No. 21, Oct. 20, 2014, pp. 26098-26102.

Thomson, S.L., et al.; "Spatially Resolved Temperature Measurement in a Liquid Using Laser Induced Phosphorescence," Journal of Fluids Engineering, vol. 123, Jun. 2001, pp. 293-302.

\* cited by examiner

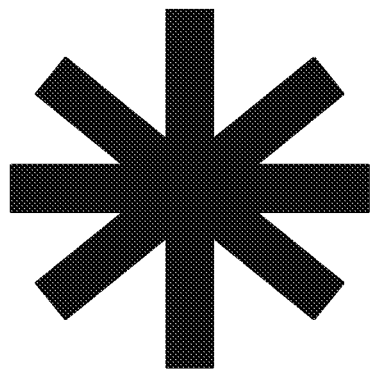
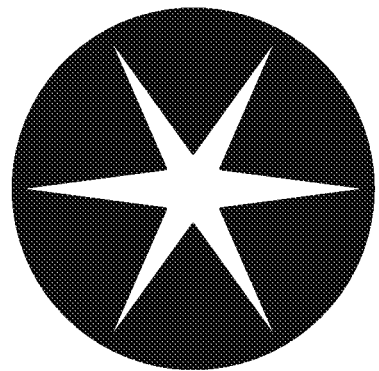
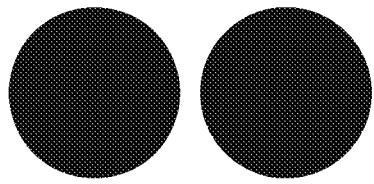
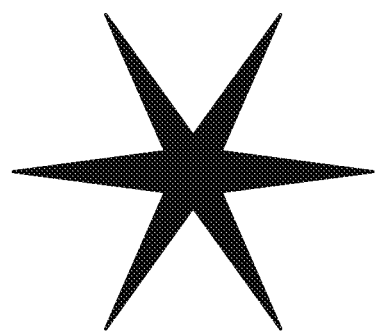
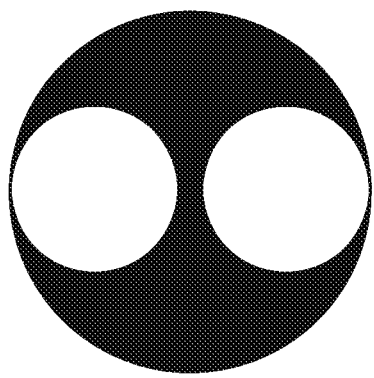
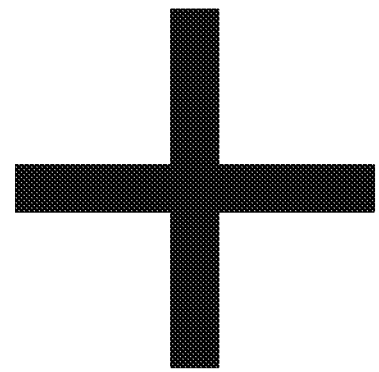
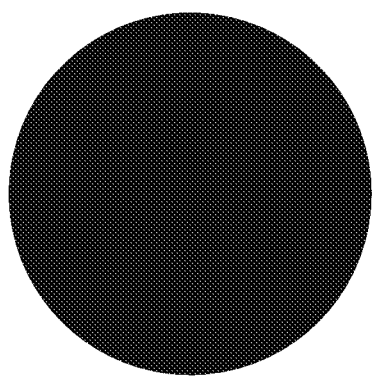
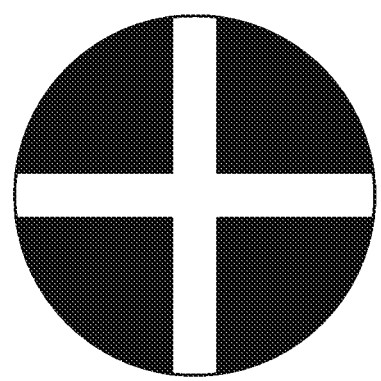

LASER SYSTEM FOR MEASURING FLUID DYNAMICS

CROSS-REFERENCE TO RELATED APPLICATIONS

This application claims the benefit of U.S. Provisional Application No. 62/294,699, filed on Feb. 12, 2016. The entire disclosure of the above application is incorporated by reference herein.

FEDERAL RIGHTS

This invention was made with government support under FA9550-14-1-0312 awarded by the Air Force Office of Scientific Research. The government has certain rights in the invention.

FIELD

The present disclosure relates to systems for measuring fluid flow and more particularly to a laser system configured to measure turbulent fluid flow.

BACKGROUND

This section provides background information related to the present disclosure which is not necessarily prior art. One of the hallmarks of turbulence is the formation of rotating currents known as vortices. Measuring the vorticity, the average angular velocity exhibited by molecules in a small cylindrical volume in space, is of great importance in fluid dynamics, especially for aerodynamic design and control of air flight. Vorticity gives the local rate of rotation of a fluid element. It plays a pivotal role in the fundamental description and understanding of fluid dynamics. Vorticity caused by airplanes increases drag and therefore results in billions of dollars in increased fuel costs and the associated use of nonrenewable resources and increased carbon footprint. Vorticity results from gradients in fluid dynamics, and is closely associated with turbulence.

Direct experimental data in thin turbulent boundary layers are difficult to obtain, and often the only source of information comes from complex computer models that have to run on supercomputers. The complexity of this problem was noted in the 1970s by Richard Feynman, who stated "Turbulence is the most important unsolved problem of classical physics". Although computer models are yielding valuable insight into the complex physics of wall-bounded turbulence, a method capable of obtaining experimental measurements of the turbulence and emergence of vorticity at a shear boundary layer would be of tremendous value for fluid dynamics, especially if results can be obtained in real time and not require months of computer time.

Vorticity is mathematically defined as the curl of the velocity vector, $\Omega = \nabla \times U$, and is physically interpreted as twice the local rotation rate (angular velocity) $\omega$ of a fluid particle, i.e. $\Omega = 2\omega$. It is one of the most dynamically important flow variables and is fundamental to the basic flow physics of many areas of fluid dynamics, including aerodynamics, turbulent flows and chaotic motion. In a turbulent flow, unsteady vortices of various scales and strengths contribute to the chaotic nature of turbulence. Even though spatially- and temporally-resolved direct measurement of instantaneous vorticity has been a long-held goal, it has proven elusive to date.

The first direct measurement of vorticity was attempted more than three decades ago by measuring the rotation rate of planar mirrors embedded in 25 µm transparent spherical beads that were suspended in a refractive-index-matched liquid. This method has rarely been utilized since the implementation of the method is very complex and the requirement of index matching significantly limits its use and prohibits its application in gas (air) flows.

Currently in all non-intrusive methods, whether particle-based, such as Laser Doppler Velocimetry (LDV) and Particle Image Velocimetry (PIV), or molecular-based, as in Molecular Tagging Velocimetry (MTV), vorticity is estimated from a number of velocity field measurements at several points near the point of interest, which then allow computation of the velocity derivatives over space. These methods provide a measurement of vorticity that is spatially averaged over the (small) spatial resolution area of each method.

Presently, experimental vortex characterization involves acquiring multiple measurements, from which the fluid velocity vectors are determined in space and used to calculate vorticity through vector (cross) product. Velocity field of a fluid flow can be obtained by analyzing images of scattered laser light with particle image velocimetry or images of phosphorescence of laser excited molecules in molecular tagging velocimetry. Fluid dynamics would be greatly enhanced if a method for vortex characterization could be developed that bypassed the determination of the velocity vector field in space but had the capability of directly determining the magnitude and sign of vorticity at a point in space.

SUMMARY

This section provides a general summary of the disclosure, and is not a comprehensive disclosure of its full scope or all of its features. The system presented according to the present teachings provides a direct and localized non-intrusive measurement of vorticity in a fluid flow using the rotational Doppler effect and Laguerre-Gaussian spatially modulated light beams that possess orbital angular momentum.

According to an embodiment, flow vorticity of a fluid is measured using light scattered from a particle suspended in a fluid. The particle is illuminated with a shaped coherent light beam having a predetermined cross sectional pattern, using a photodiode, a signal from light from the particle is collected for a predetermined length of time. This collected signal is subjected to an FFT that decomposes the signal into a power spectrum. The decomposed signal presents the vorticity of the fluid at the measured point.

According to another embodiment, the system for measuring fluid dynamics measures a group of µm sized microparticles to obtain the average fluid rotation rate about the beam optical axis within a µm sized illumination region. The spatially-averaged vorticity within the µm sized illumination region is calculated. In another embodiment, the spatially-averaged vorticity in a fluid is obtained by measuring the angular velocity of a single particle having a size between 2 µm and 150 µm at a focal point of a shaped laser beam.

In another embodiment, the spatially-averaged vorticity in an unsteady fluid flow with spatially varying vorticity field fluid is obtained by measuring reflected or emitted light from a particle with a photodiode. The system calculates the angular velocity of a single suspended particle at a focal point of a shaped the laser beam. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 5A-5H represent alternate laser beam cross sections for a beam used in the system shown in FIG. 1A;

Corresponding reference numerals indicate corresponding parts throughout the several views of the drawings.

DETAILED DESCRIPTION

Figure 1A:
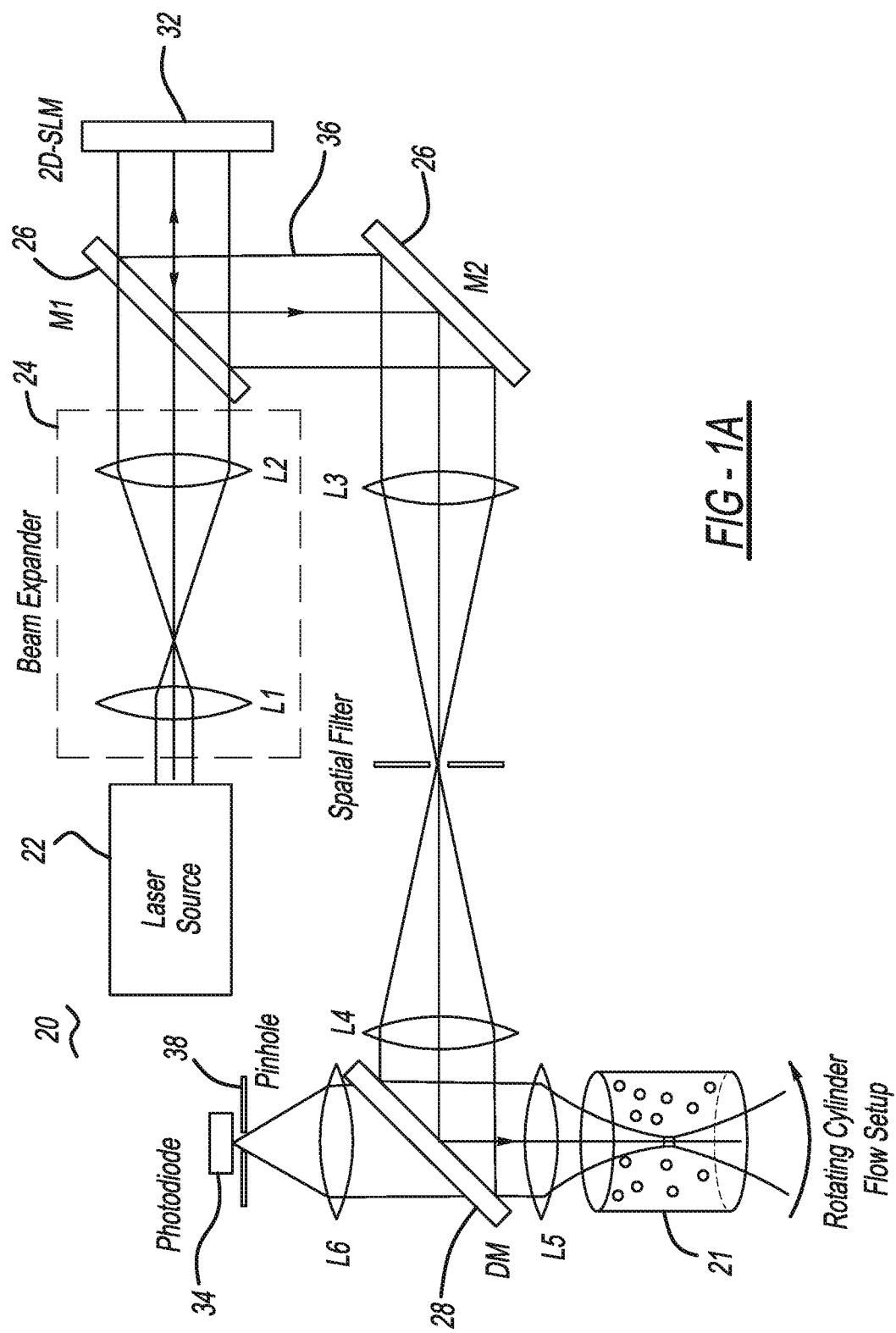
FIGS. 1A-1C represent the system for measuring fluid vorticity according to the present teachings.

Example embodiments will now be described more fully with reference to the accompanying drawings. FIGS. 1A and 6-11 represent systems 20 for measuring fluid movement according to the present teachings. Specifically, the systems 20 for measuring fluid dynamics represent optical configurations for measuring fluid vorticity at one or more point locations within a fluid flow 21. As shown in FIG. 1A, the system 20 has a laser source 22, and optical expander 24, beam splitter mirrors M1-M2 26; DM, dichroic mirror 28; associated lenses, L1-L6 30; and utilizes computer controlled 2D spatial light modulators (SLM) 32, configured to introduce complex phase designs, and photodiodes 34.

Figure 1B:
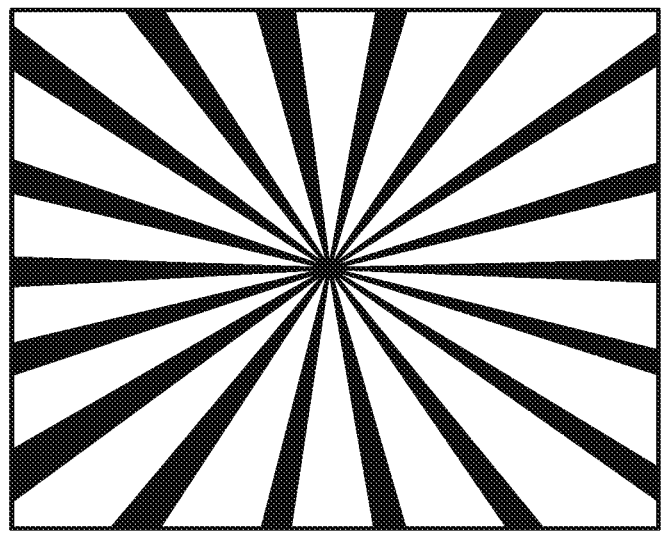
Figure 1C:
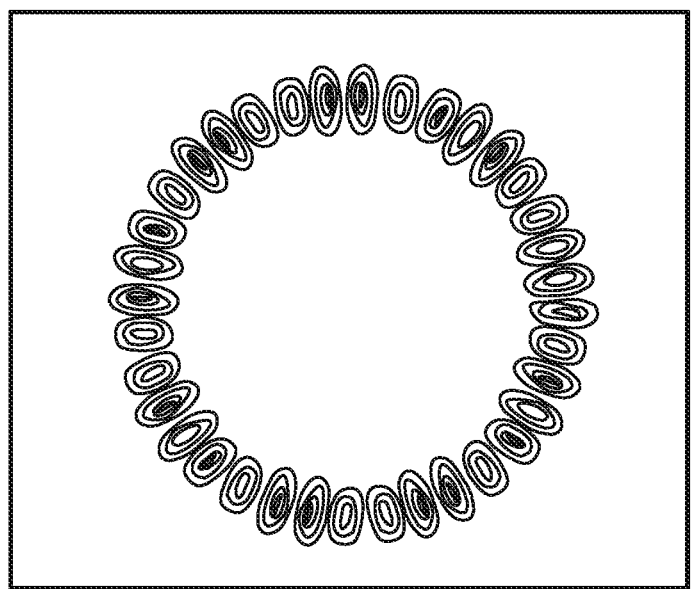

FIG. 1B represents a resulting beam structure used to illuminate particles in fluid flow in the form of a diffraction pattern displayed on 2D White spatial light modulators 32 where white corresponds to 0 phase shift while black corresponds to $2\pi$ phase shift with 256 steps in between. The present diffraction pattern has multiple, generally triangular stripes, outwardly expanding in a radial manner from a center point. The stripes preferably have straight edges. This diffraction pattern can be used in the systems shown in FIGS. 1A, 8 and 11. FIG. 1C represents the wave form resulting from the Laguerre-Gaussian spatially modulated light beam 36 used in FIGS. 1A, 8 and 11.

For the measurements presented, an Optical Angular Momentum (OAM) laser beam 36 has an optical angular momentum with $l=\pm 18$, resulting in 36 bright features (petals). Scattering from objects rotating at angular velocity $\omega$ (or rotation frequency f) leads to intensity modulation at frequency $f_{mod}=36\omega/2\pi=36f$. It should be understood that a beam with $l<\pm 18$ or $l>\pm 18$ can be used by the system 20.

The system 20 functions to perform a direct non-intrusive measurement of vorticity using a laser-based method that is sensitive to rotational motion in a fluid. Translational velocities can be measured with Laser Doppler Velocimetry (LDV) by taking advantage of the (linear) Doppler effect, which causes a frequency shift when objects move towards or away from a source of light. Analogously, the rotational Doppler effect can be used to measure the angular velocity of a rotating object. The system 20 employs the rotational Doppler effect using the Laguerre-Gaussian (LG) light beams that possess orbital angular momentum and a spatial (azimuthal) modulation of the beam phase front. The creation of beams with arbitrary orbital angular momentum l, or beams having a superposition of counter-rotating optical angular momentum ($\pm l$), utilizes the computer controlled 2D spatial light modulators 32 capable of introducing complex phase designs.

The system provides a direct vorticity measurement in a fluid flow based on angular velocity measurement of micron-sized particles free flowing in the fluid using rotational Doppler effect and rotational Doppler effect laser beams with optical angular momentum. The very small particles faithfully track the fluid flow and, at a steady state, they move with the local flow speed and rotate with the local angular velocity of the fluid (or half the local flow vorticity at the particle center).

The system is applied to rotating fluids in a flow field known as solid body rotation or rigid body flow field—for which the angular rotational velocity is uniform and particles carried by the flow also rotate about their center as if they were part of the rigid body. In this type of flow, the vorticity is the same everywhere. As show in FIGS. 2A-4, data from two example systems are presented. In the first, the signal from a group of 6 µm microparticles is integrated to obtain the average fluid rotation rate about the beam optical axis within a 100 µm illumination region, thus obtaining the spatially-averaged vorticity within that region. In the second experiment, the same information is obtained by measuring the angular velocity of a single 100 µm particle in the flow. The latter is the type of transient measurement required to determine vorticity in more complex flows fields.

The system 20 for measuring the local flow angular velocity and vorticity is shown in FIG. 1A and discussed in greater detail as follows. A 488 nm continuous wave beam 36 from an optically pumped semiconductor laser 22 (Genesis MX, Coherent, USA), with an initially Gaussian beam profile, is expanded by a telescope (L1, L2) within the expander 24 and shaped by a two-dimensional liquid crystal on the silicon spatial light modulator (SLM) 32 (LCOS-SLM, Hamamatsu, Japan). The SLM 32 is programmed with a diffraction pattern, as shown in FIG. 1B, that introduces the rotational Doppler effect spatial modulation and diffracts the spatially shaped beam. The shaped beam possesses the orbital angular momentum corresponding to a superposition of rotational Doppler effect$\pm 18$ modes, and its far-field intensity profile corresponds to the circular periodic structure with the 36 petals, as shown in FIG. 1C.

The beam 36 is then focused with long focal length lens L3 and a first diffraction order is selected with an aperture. Lens L4 collimates the beam, which after reflection from dichroic mirror (DM) 28 is focused by lens L5 (having a 60 mm focal length) into the center of a rotating cylindrical container of fluid 21 with the beam optical axis aligned along the rotation axis. The fluid container term is used herein to include an enclosed tank, an open ended pipe, a conduit, a beaker or the like. The beam 36 diameter at the focus is measured to be about 120 µm and the average power is 12 mW, an intensity that is at least one order of magnitude too weak for causing laser trapping.

The container is filled with fluorescent micro-particles suspended in a density matched solution (for example, water and glycerin having density about 1.05). Two sets of red fluorescent polymer microspheres (for example, obtained from Thermo Fisher Scientific Inc.) are used in these measurements, one with a 6 µm diameter (15% variance) and the other with a 100 µm diameter (7% variance). The container cap is fitted with a thin quartz window that touches the liquid surface at all times to eliminate free surface effects. The angular velocity ω of the container is controlled by an optically encoded motor (3501 Optical Chopper, New Focus, USA) rotating at frequency f and angular velocity ω=2πf. Measurements (see FIGS. 2A-4) were done after the container was spun for a few minutes to ensure a steady state rotation flow field had been established. The resulting flow field is devoid of any secondary flow and is precisely characterized by the solid-body rotation velocity field U=r×ω and its spatially uniform vorticity field Ω=2ω.

Epi-directional fluorescent light from the irradiated particles is collected with lens L6 and is focused onto a photodiode detector or sensor 34. A small diameter pinhole 38 is set before photodiode in order to spatially filter out the desired signal from outside of the focal volume in the fluid. The intensity-modulated signal from the fluorescent particles can be recorded at a 10 kHz sampling rate and spectrally analyzed by a programmable computer controller 90 (see FIG. 15). The controller 90 includes a microprocessor and memory for running software programming instructions including the algorithms disclosed herein and for making the appropriate measurements, calculations and determinations related to velocity, vorticity, turbulence, magnitude and direction of the fluid flow sample. The use of epi directional detection and the use of fluorescent particles, in combination with clean optical angular momentum shaped laser excitation, allows the rejection of scattered light from the rotating surfaces of the container and guarantees the measured signal originates from within the rotating body of fluid.

Figure 2A:
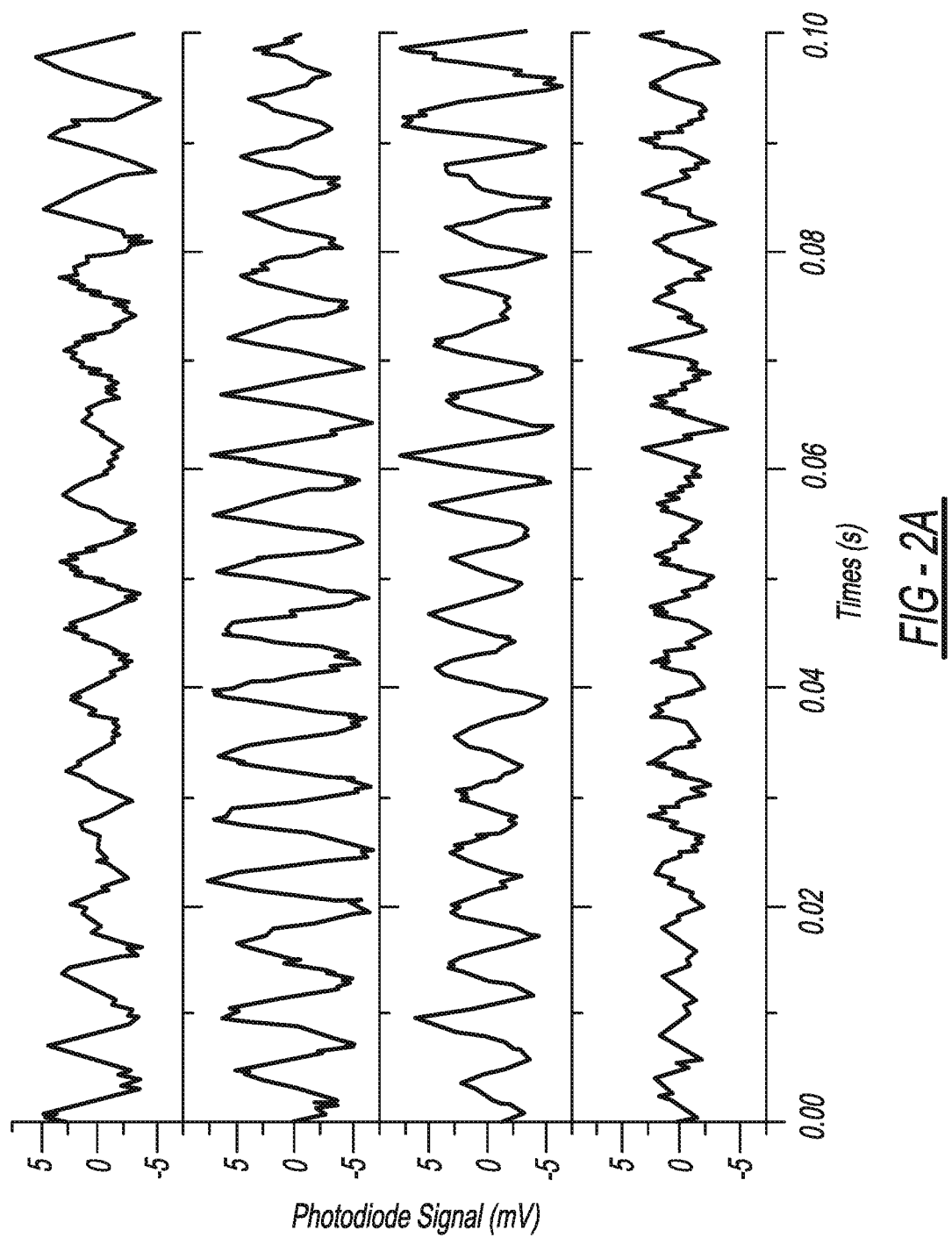
FIGS. 2A-4 represent measured and calculated signals from the system shown in FIG. 1A.
Figure 2B:
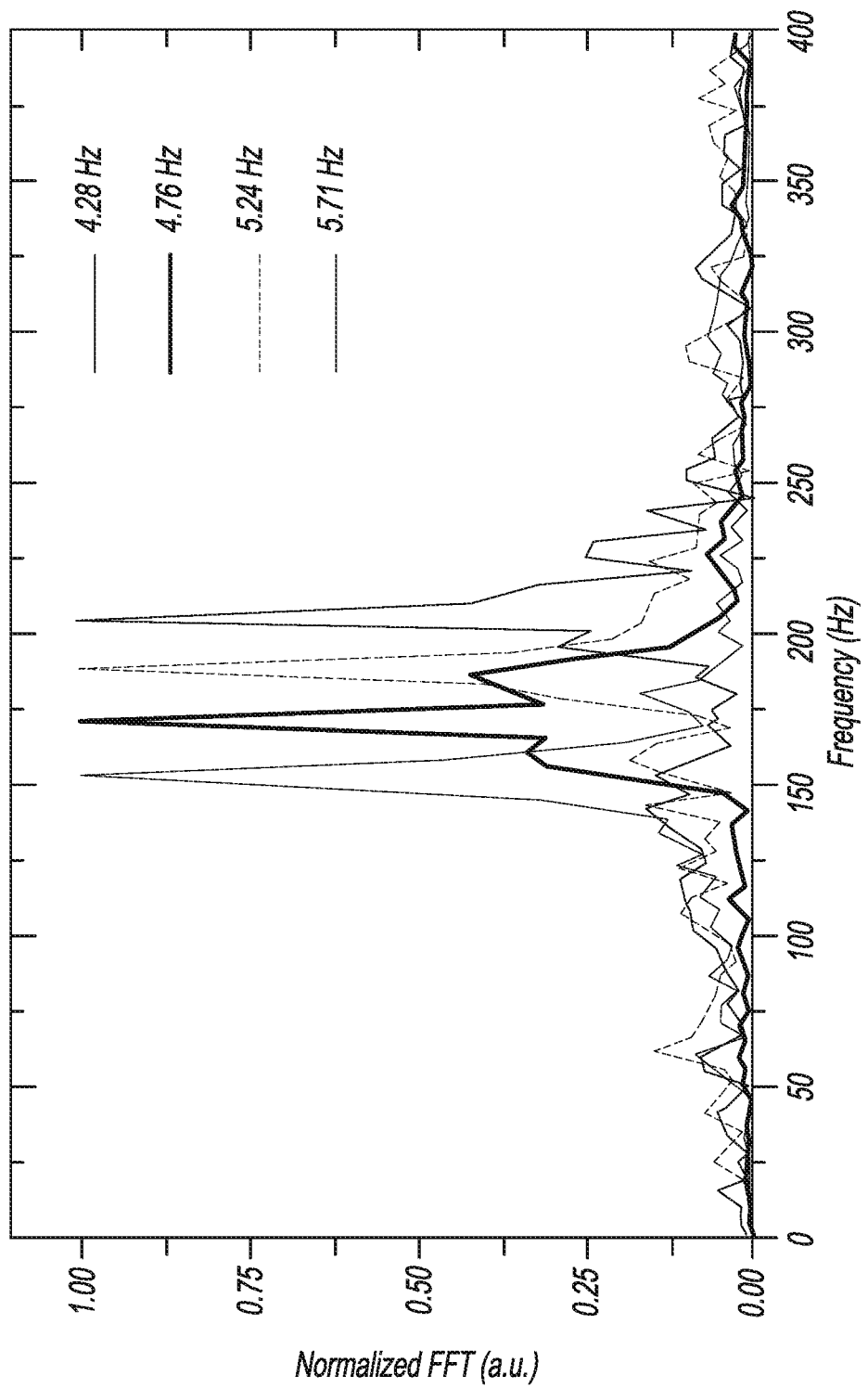

The first set of data in FIGS. 2A and 2B show the measurement with 6 µm fluorescent particles. In this case, by measuring the rotation rate of an ensemble of particles within the ≈100 µm beam diameter, the averaged fluid rotation rate is obtained within that region. FIG. 2A shows examples of intensity modulation of collected (AC-coupled) signals for four different prescribed rotation frequencies of the cylindrical container with f=4.28 Hz, 4.76 Hz, 5.24 Hz and 5.71 Hz. Fourier transforms of each signal provides the spectral information in FIG. 2B using a short data record of about 200 ms in length.

From the spectral peaks in FIG. 2B the modulation frequencies for the four cases are 154.16±5 Hz, 171.37±5 Hz, 188.58±5 Hz, and 205.76±5 Hz. These values correspond to the measured fluid rotation rates of 4.28±0.14 Hz, 4.76±0.14 Hz, 5.24±0.14 Hz, and 5.72±0.14 Hz, respectively. These values are in excellent agreement with the prescribed rotation frequencies of the rotating fluid container. Accuracy of these measurements is limited by FFT resolution divided by two-times the optical angular momentum. For a 200 ms data record, an optical angular momentum with l=±18 is obtained 5/36=0.14 Hz. Given the steady flow field in this experiment, one can improve the measurement accuracy, if desired, by increasing the length of the data record for FFT analysis or increasing the beam's optical angular momentum. For arbitrary flows, one could speed up data acquisition to 20 ms, reducing accuracy to 1.4 Hz.

A second set of example measurements was conducted on larger 100 µm particles with low particle density in solution to ensure single particle measurement within the ≈100 µm beam diameter. The data was confirmed by visually observing the single particle presence in the focal volume of structured laser beam based on its intensity time series during data collection.

Figure 3:
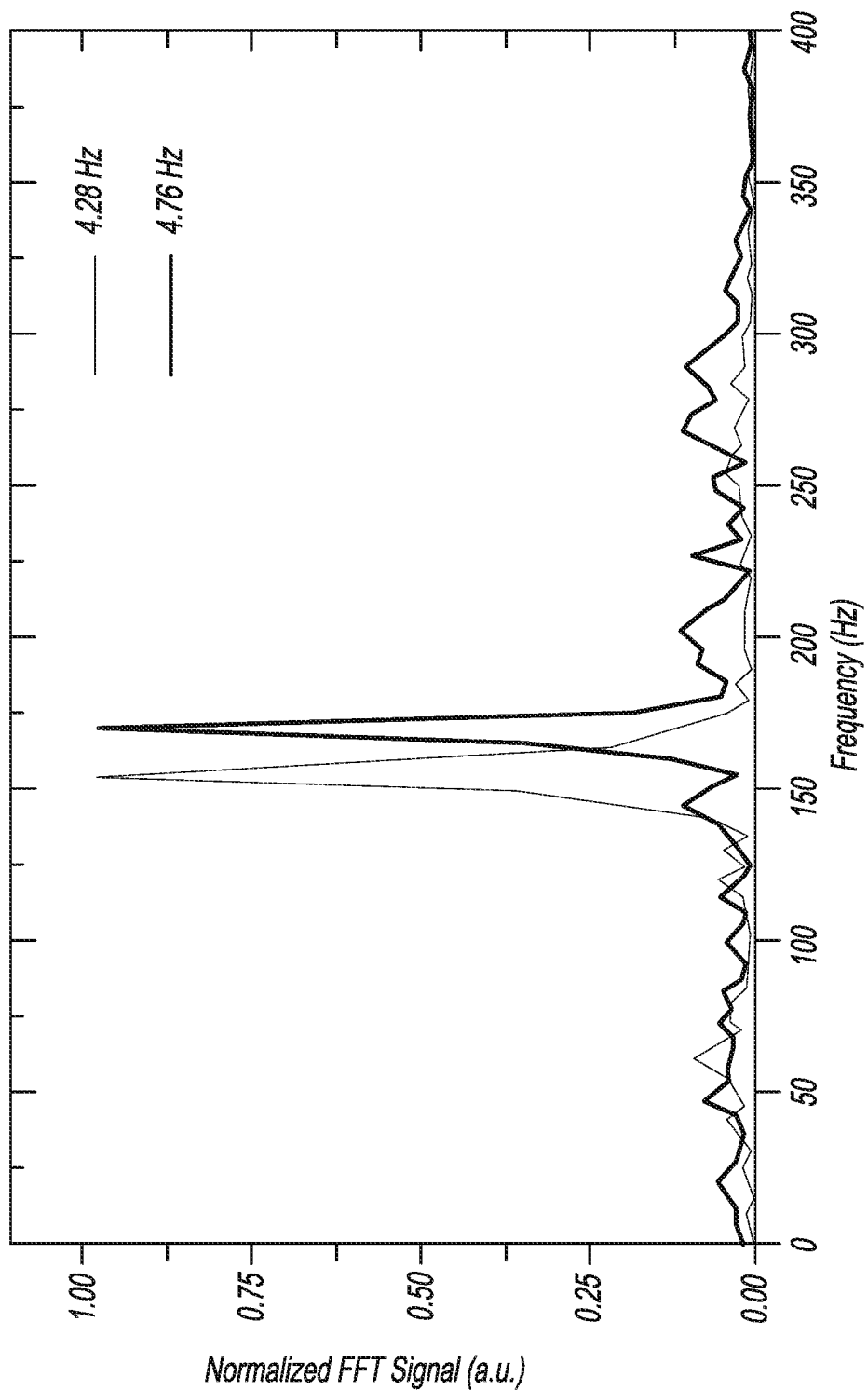

As shown in FIG. 3, FFT analysis was conducted for two different prescribed rotation frequencies of the cylindrical container, f=4.28 Hz and 4.76 Hz (200 ms data record). The peaks indicate modulation frequencies of 154.08±5 Hz, and 170.10±5 Hz for these two cases. The corresponding values of the measured fluid rotation rates are 4.28±0.14 Hz, 4.73±0.14 Hz, which are again in excellent agreement with the imposed rotation frequencies of the rotating fluid container.

The solid body rotation flow field was selected for these proof-of-concept experiments because it is relatively simple to create and has well-characterized velocity and vorticity fields. When the liquid-filled cylindrical container, initially at rest, starts to spin, the fluid layer near the moving wall starts to move with the cylinder due to the no-slip viscous boundary condition at the wall. The motion is then propagated throughout the container by viscous shear until the entire body of liquid rotates at the same speed of the container.

The final steady state velocity field is that of solid body rotation with vorticity that is constant in time and uniform in space, with an axis parallel to the axis of rotation of cylinder and magnitude equal to twice the cylinder angular velocity. While a vorticity measurement using laser beams with optical angular momentum in a steady flow environment has been conducted, it is envisioned that the present teachings can be applied to the measurement of unsteady flows. For micro particles in a Stokes flow regime, particle rotation time can be estimated from $\tau=\rho_p d^2/60\mu$, where $\rho_p$ and d are the particle density and diameter, and µ is the fluid viscosity. For 100 µm particles like the rotation time is about 100 µsec. Therefore, unsteady vorticity measurements are feasible and could be obtained by acquiring shorter record lengths of data. Because of the quadratic dependence of particle rotation time on diameter, one can select the appropriate particle size to ensure a response time that is faster than the flow-fluctuation time scale.

Figure 4:
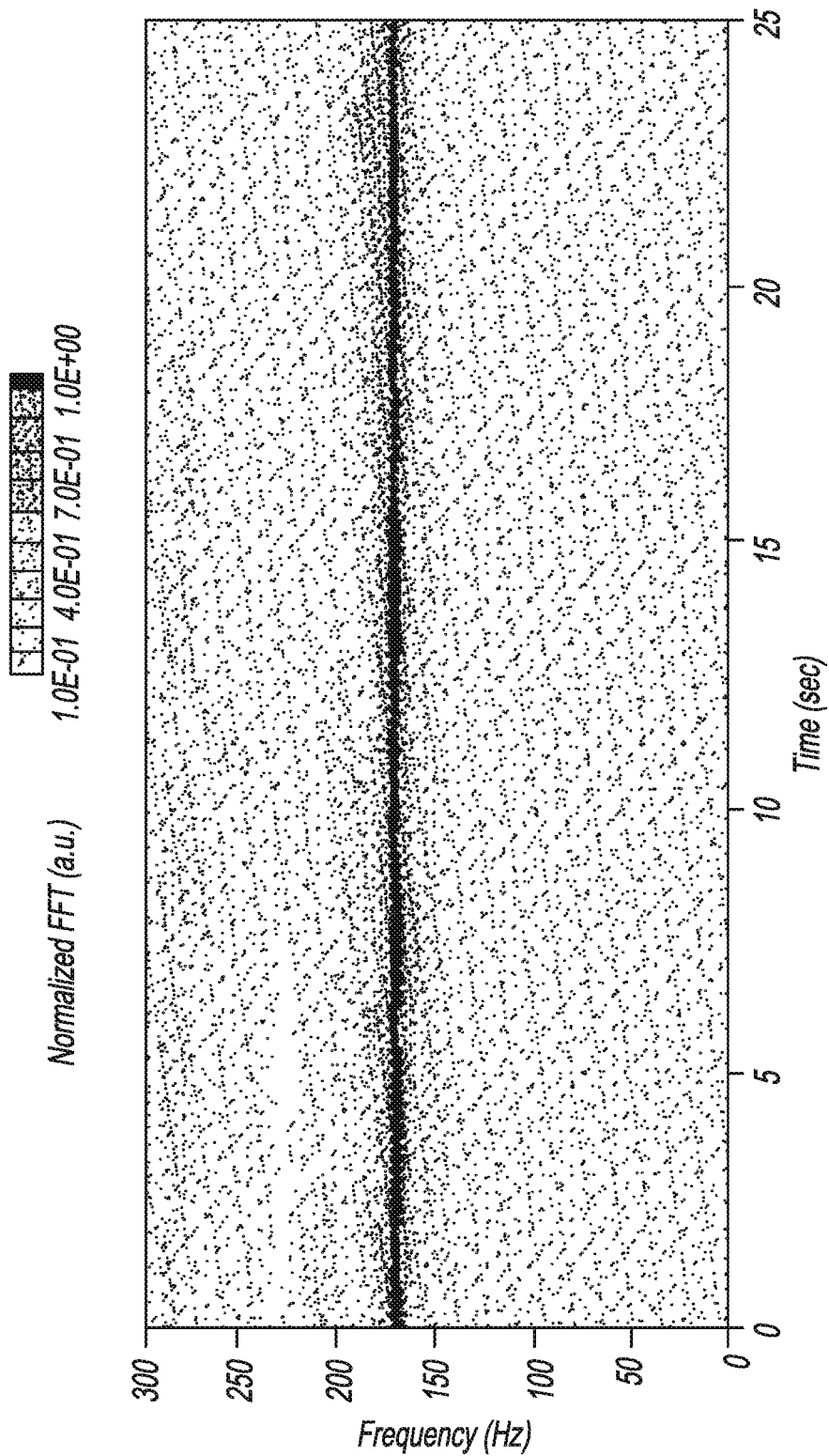

FIG. 4 depicts the time invariant spectral peak (200 ms FFT window) in from a 100 µm particle that lingers within laser illumination at the axis of the rotating container while spinning with the fluid rotation rate. Shown is an FFT map of a signal for a single 100 µm particle in solution over time, with the solution rotating at f=4.76 Hz. Measuring the spectral peak based on the 40 s data record yields a modulation frequency of 171.5±0.025 Hz, or particle/fluid rotation rate of 4.76 Hz, in perfect agreement with the imposed rotation frequency of the fluid container.

FIGS. 5B-5G represent alternately shaped laser beam cross sections for a beam used in the system shown in FIG. 1. These beam shapes can be created using a 2D-SLM or diffractive optics. Alternative to LG or OAM beams, the alternate laser beam 36 cross sections shown in FIGS. 5B-5G can be used to make vorticity measurements. These beams will have a beam diameter at the focus which is measured to be between about a few microns to a few centimeters, or preferably about 120 µm and the average power of between 0.01 to 1 W/cm^2, an intensity that is at least one order of magnitude too weak for causing laser trapping. The system can use a static beam pattern to determine the magnitude of the fluid rotation. To determine the direction of the beam pattern in addition to its magnitude, the beam 36 having a shaped cross section can be rotated with respect to the rotating fluid. This rotation of the beam can have a different rotational frequency than the rotational frequency of the fluid. With the resulting signal being additive with the rotational frequency of the fluid in one direction and subtractive in an opposite direction.

In this regard, the use of Optical Angular Momentum, or Laguerre-Gaussian, or azimuthally structured laser beams with counter-rotating optical angular momentum (±l) can determine the angular speed of rotating objects based on rotational Doppler effect. When the illumination comprises two helically phased beams of opposite values of l, their scattering into a common detection mode gives opposite frequency shifts resulting in an intensity modulation of frequency $f_{mod}=2|l|\omega/2\pi$, where ω is the angular velocity of the rotating object. The same concepts can be employed to spin and to measure the angular velocity of a microparticle trapped and spinning in an optical trap.

Figure 6:
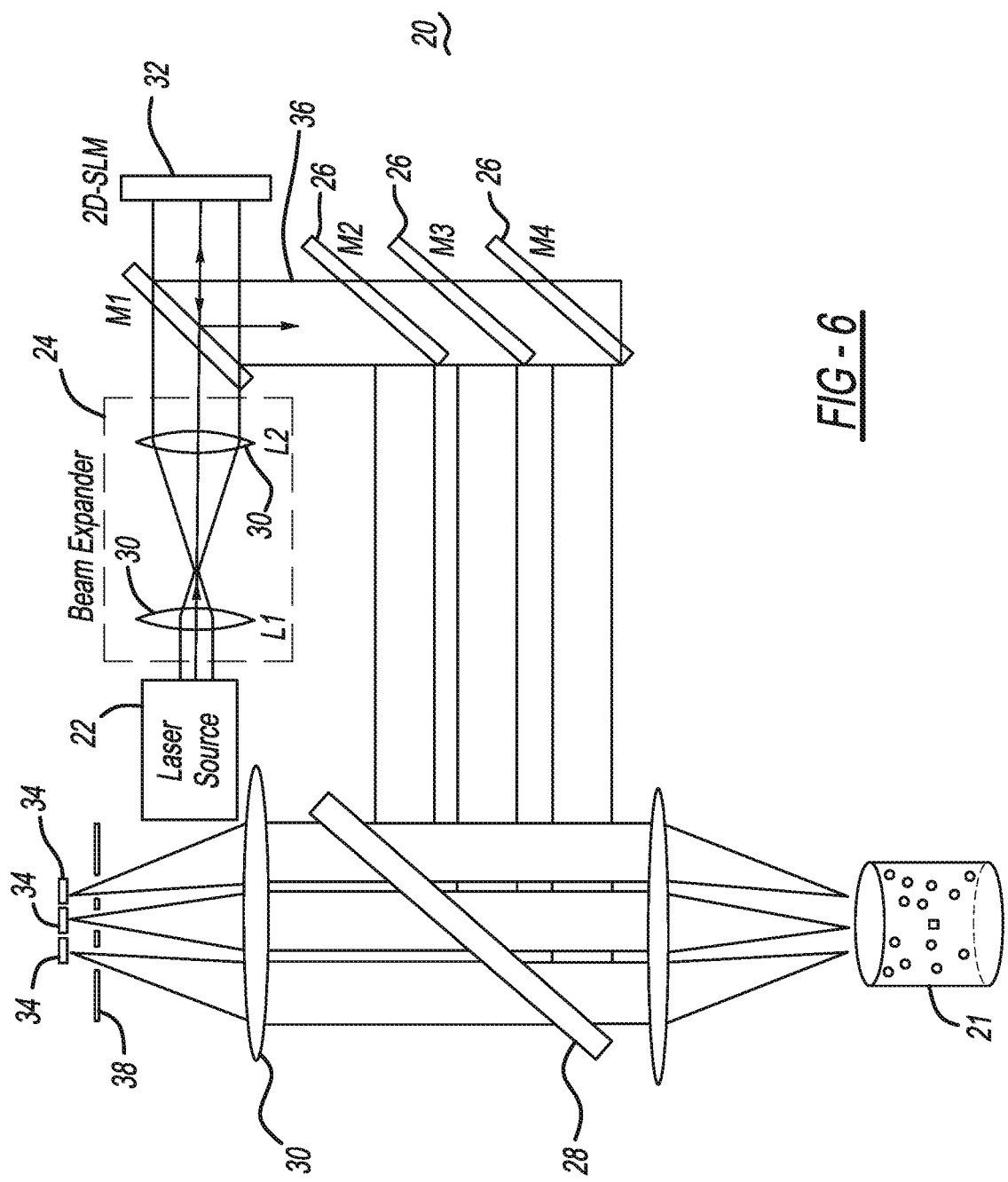
FIG. 6 represents an alternate fluid measuring system configured to evaluate the vorticity of a fluid at a plurality of locations in a fluid flow.

FIG. 6 represents an alternate fluid measuring system 20 configured to evaluate the vorticity at a plurality of locations in a fluid flow. As shown in FIG. 6, the system 20 has a laser source 22, and optical beam expander 24, beam splitter mirrors M1-M4 26; DM, dichroic mirror 28; associated lenses, L1-L6 30; and utilizes computer controlled 2D spatial light modulators (SLM) 32 configured to introduce complex phase designs. As can be seen, the beam splitting mirrors M2-M4 direct three (or more) separate shaped beams 36 into the fluid sample 21. The reflected or emitted beams from the particle or particles are then collected by an array of photodiodes 34.

Figure 7:
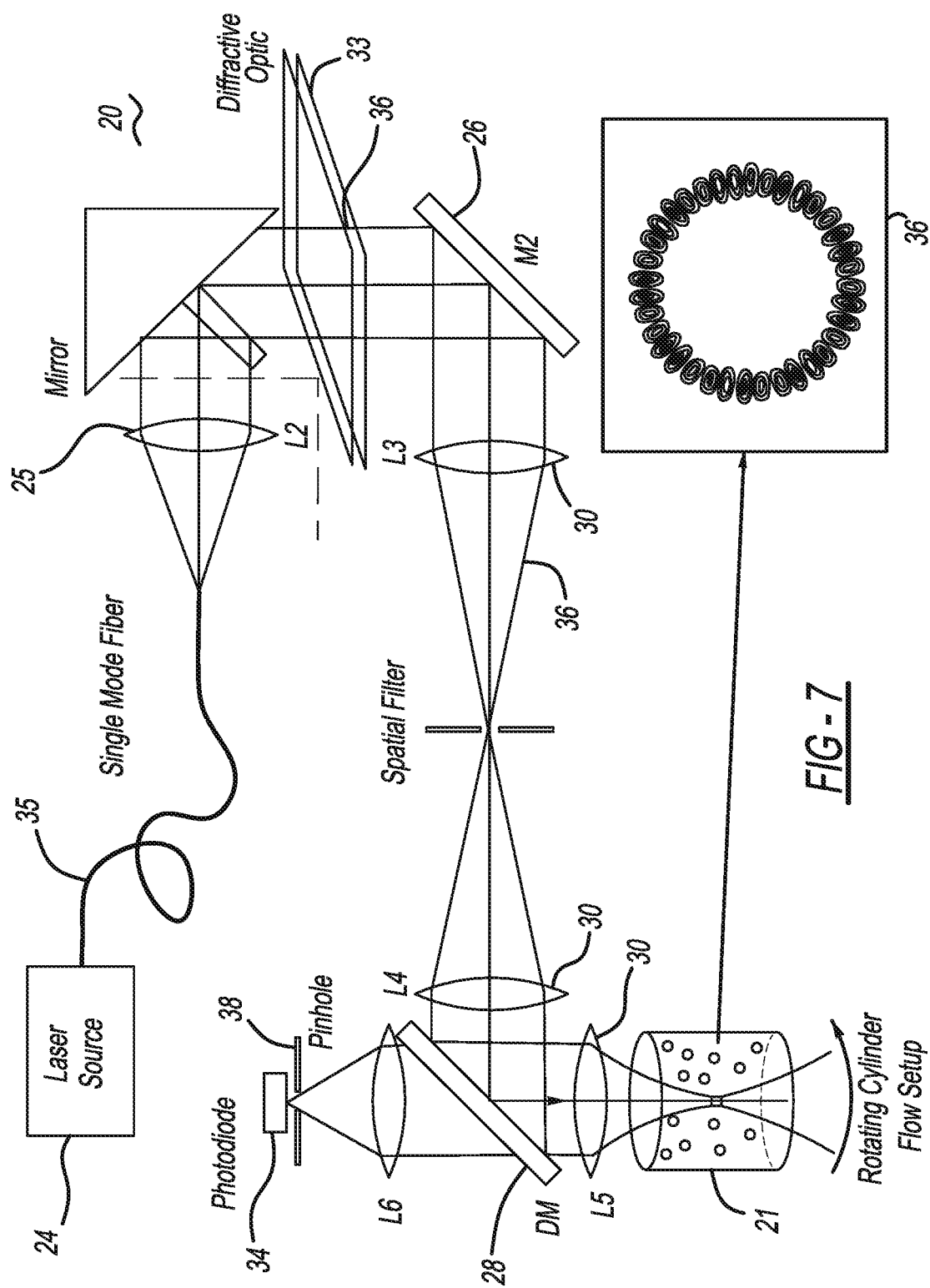
FIG. 7 represents an alternate fluid measuring system configured to evaluate the vorticity of a fluid using a fiber laser source and a diffractive optic.
Figure 8:
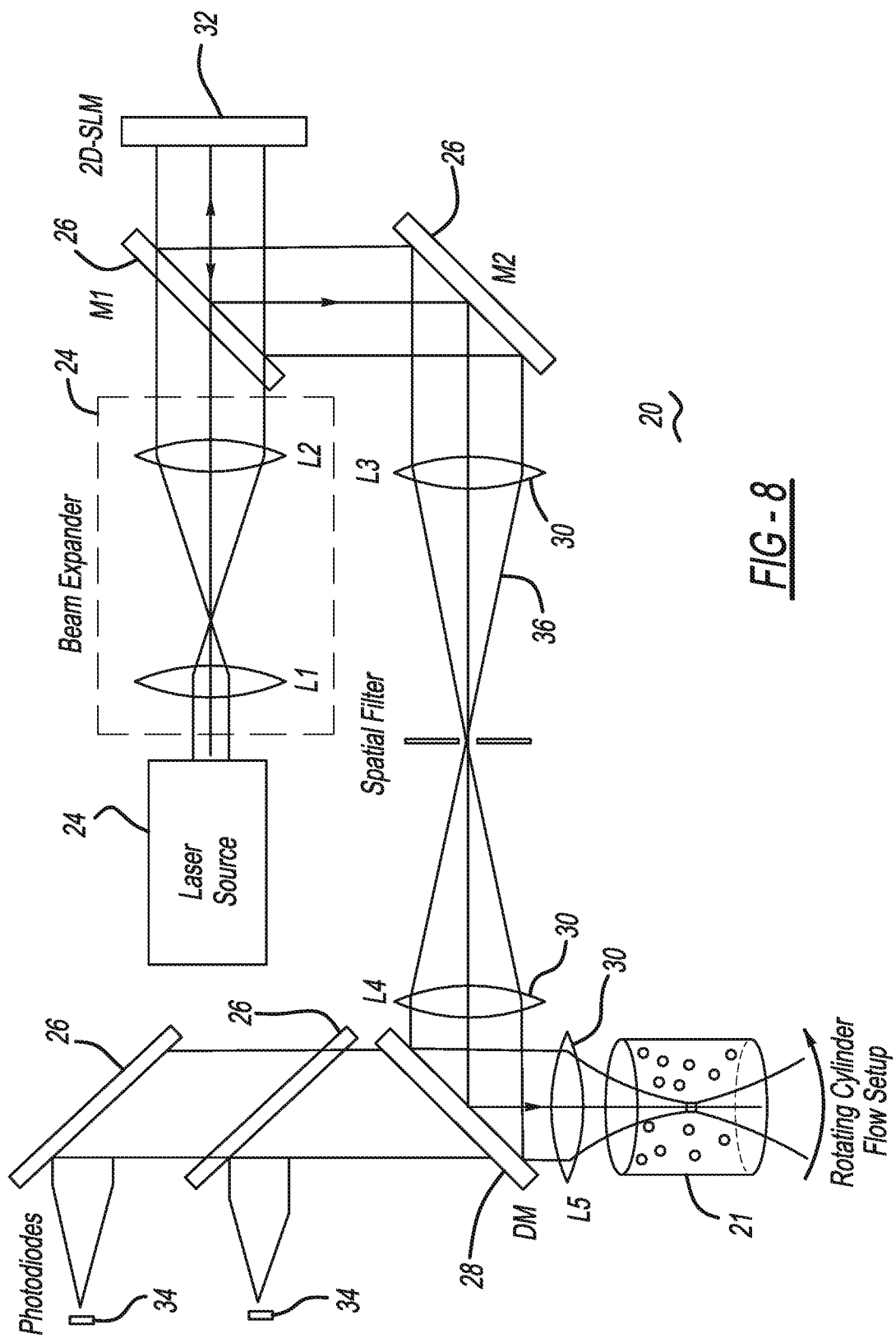
FIG. 8 represents an alternate fluid measuring system configured to evaluate the vorticity using a plurality of emission colors.

FIG. 7 represents an alternate fluid measuring system configured to evaluate the vorticity using a fiber laser source 24 and a diffractive optic 33. As shown in FIG. 7, the system 20 has a laser source 22 which utilizes a single mode fiber 35 to clean the spatial mode of the laser beam. The beam 36 from the laser source 24 and a collimating lens 25 are positioned in relation to a fiber end, and the system also employs beam splitter mirrors M1-M2 26; DM, dichroic mirror 28; and associated lenses, L1-L6 30. The diffractive optic 33 can be a computer controlled 2D spatial light modulators (configured to introduce complex phase and amplitude designs). This will allow the rotation of the beam 36 with relation to the fluid sample 21. As described above, light from the particle is collected with a photodiode 34 and computer processed with an FFT enabled chip FIG. 8 represents an alternate fluid measuring system configured to evaluate the vorticity using a plurality of emission colors from different types of particles. In this regard, the fluid 21 can have suspended microspheres which fluoresce with different colors. As shown in FIG. 8, the system 20 has a laser source 22, and optical beam expander 24, beam splitter mirrors M1-M2; DM, dichroic mirror 28; associated lenses, L1-L6 30; and utilizes a computer controlled 2D spatial light modulator (SLM) 32 configured to introduce complex phase designs. The different signals can be separated using filtered beam splitter mirrors 26 and detected by separate photodiodes 34.

Figure 9:
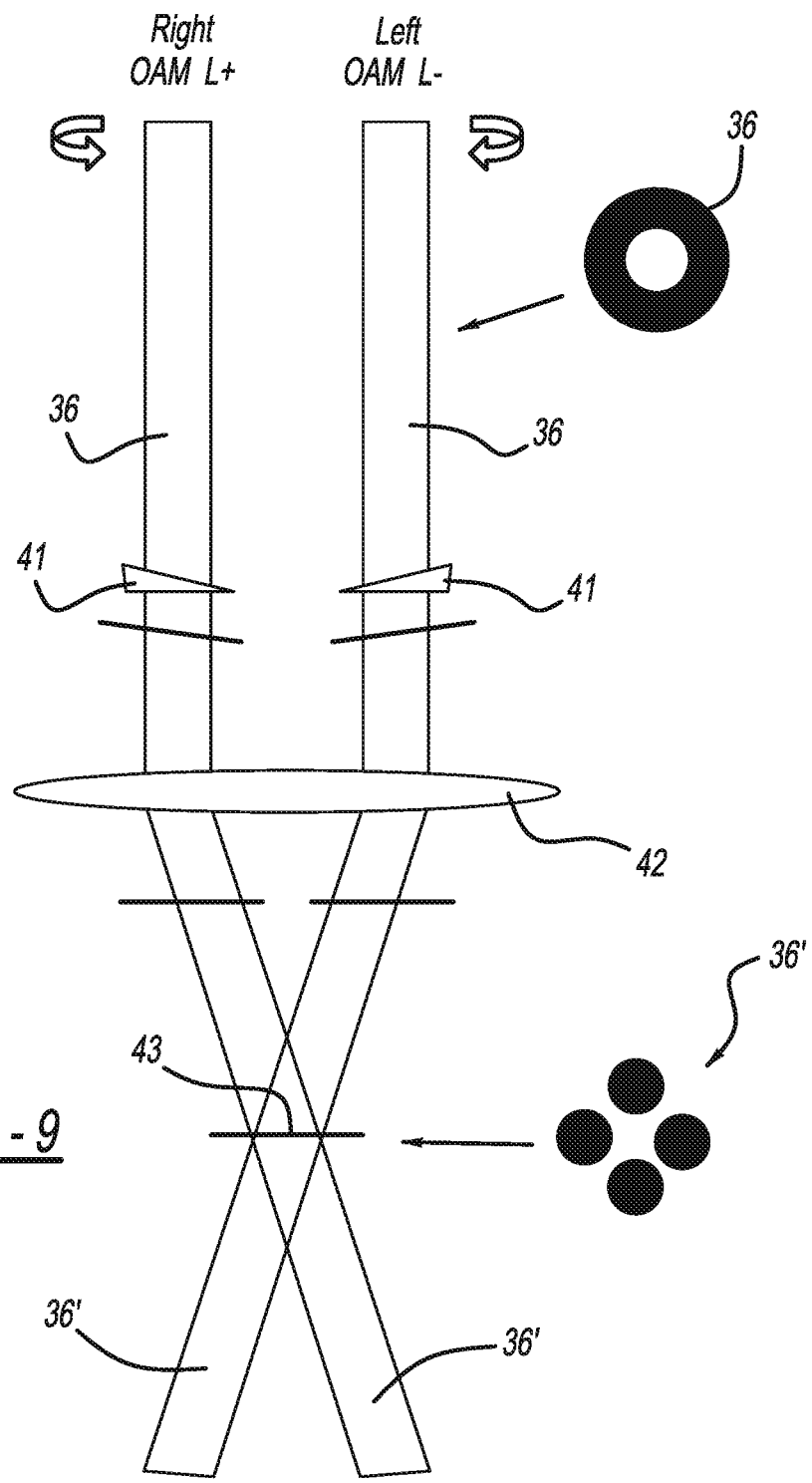
FIG. 9 represents a portion of an alternate fluid measuring system configured to evaluate the vorticity using a pair of intersecting shaped coherent light beams.

FIG. 9 represents an alternate fluid measuring system configured to evaluate the vorticity using a pair of intersecting beams. The system 20 as described above has a laser source 22, and optical expander 24, beam splitter mirrors M1-M2 26; DM, dichroic mirror 28; associated lenses, L1-L6 30; and utilizes a computer controlled 2D spatial light modulator (SLM) 28 configured to introduce complex phase designs. The phase fronts of the two beams 36 are adjusted using optical wedges 41 so that at the focus location 42, the two laser beams 36 have parallel wave or phase fronts. Beams 36 with only one sign of angular momentum look like an annular ring or donut with a void or hole in the center. But at a point of crossing 43, the two beams 36' interfere and create a positive or negative superposition that make bright and dark regions; here shown as four spaced apart dark dots for +2 and −2. Spatial light modulators (SLM) 28 are used to rotate one beam front with respect to the other beam front. As described above, this configuration allows the direction as well of the magnitude of vorticity to be calculated.

Figure 10:
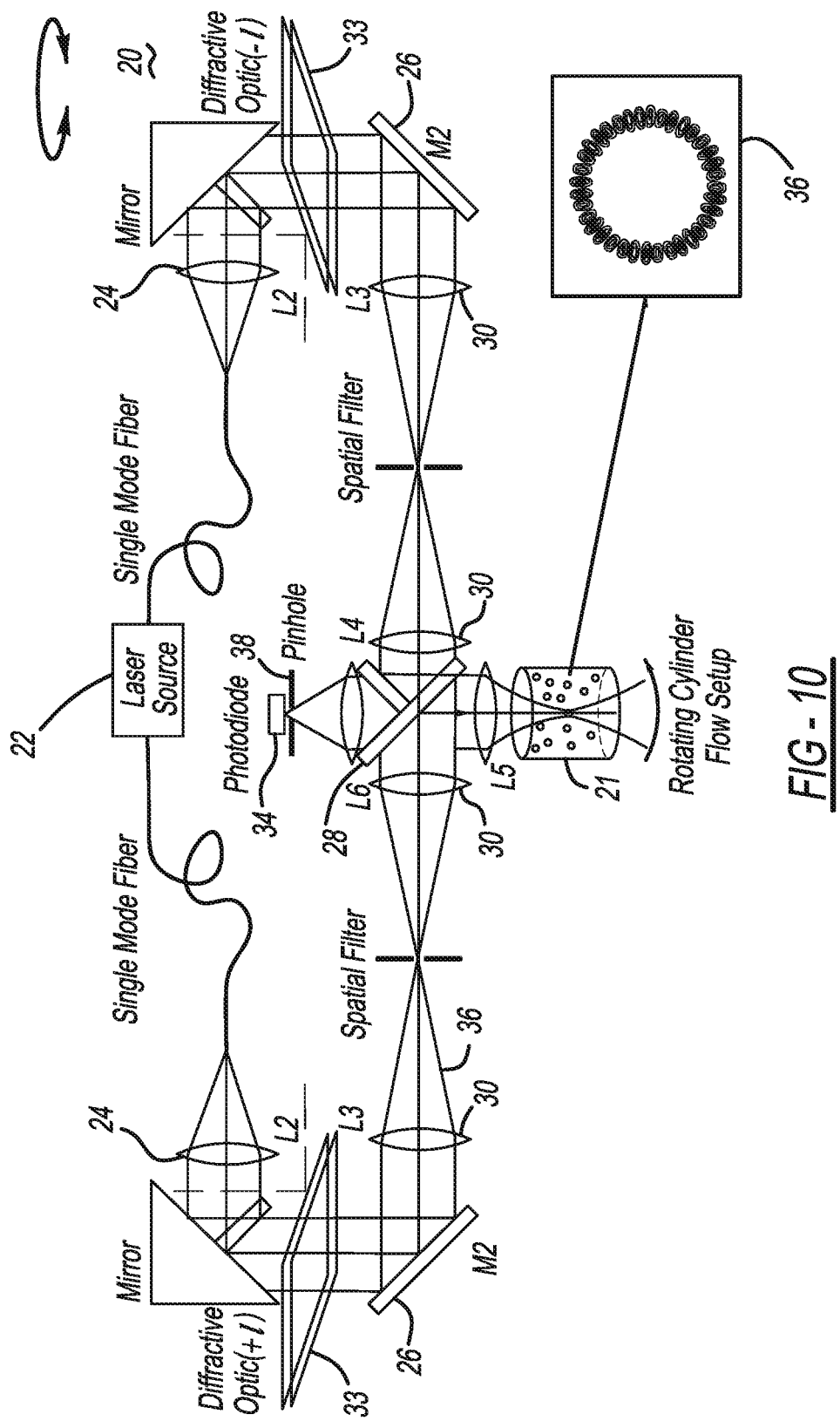
FIG. 10 represents an alternate fluid measuring system configured to evaluate the vorticity of a fluid using a pair of collinear light beams.

FIG. 10 represents an alternate fluid measuring system configured to evaluate the vorticity using a pair of intersecting overlapping collinear beams. As shown in FIG. 10, the system 20 has a laser source 22 using an inexpensive fiber optic 35 conditioner, beam splitter mirrors M1-M2 26; DM, dichroic mirror; associated lenses, L1-L6 24 and 30; and utilizes computer controlled diffractive optics 33 configured to introduce complex phase designs. Rotating one of the optics can give the sign of the rotational direction of the field. Additionally, modulating the beam using an acoustic-optic modulator will allow calculation of the sign of rotation of the fluid.

Figure 11:
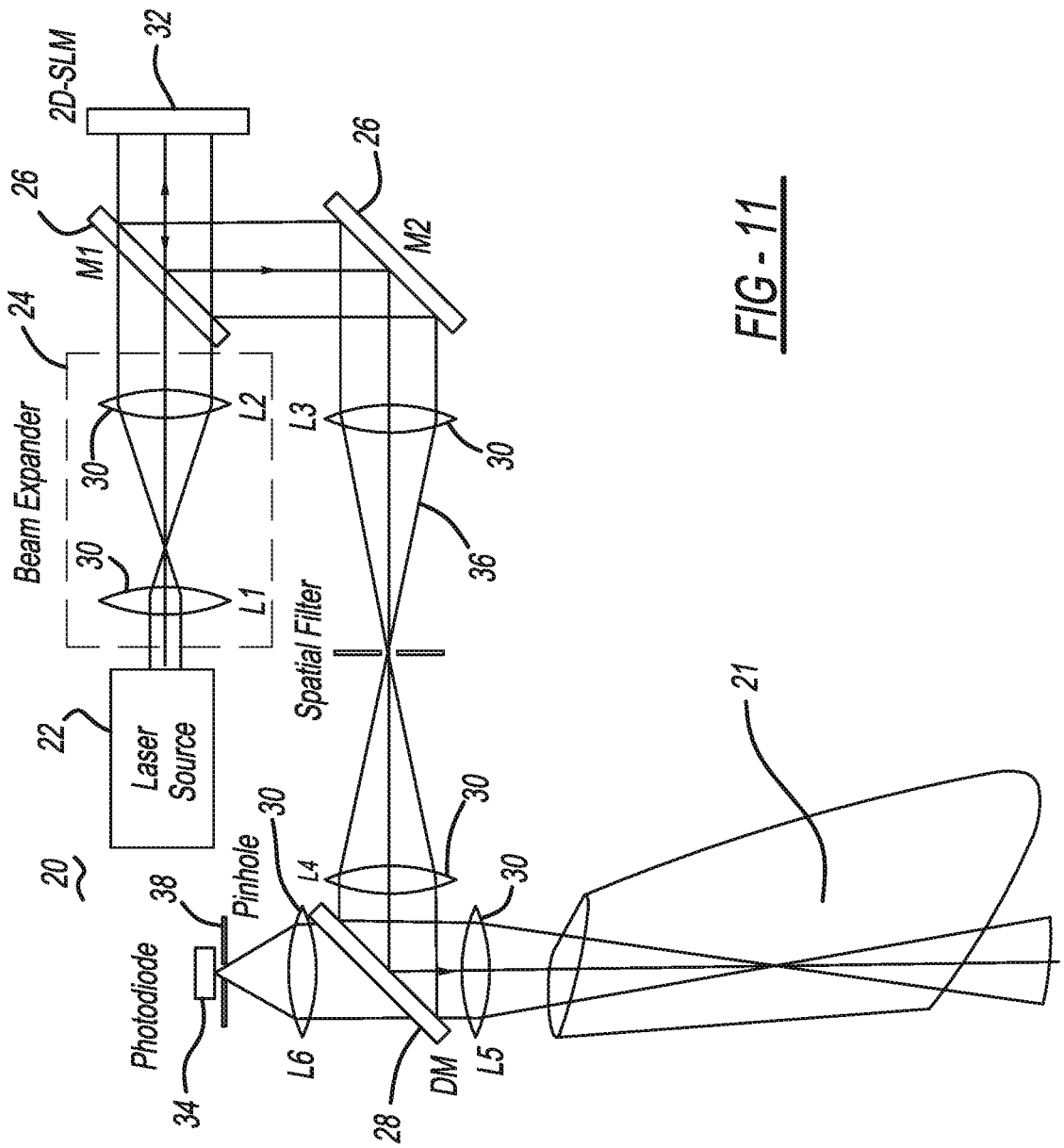
FIG. 11 represents the system according to FIG. 1A for measuring fluid vorticity near the surface of a structure.

FIG. 11 represents the system according to FIG. 1A for measuring fluid vorticity near the surface of a structure. The system 20 can use a 488 nm continuous wave beam 36 from an optically pumped semiconductor laser 22 (Genesis MX, Coherent, USA). The initially Gaussian beam profile is expanded by a telescope 24 (L1, L2) and shaped by a two-dimensional liquid crystal on a silicon spatial light modulator 32 (LCOS-SLM, Hamamatsu, Japan). The SLM 32 is programmed with a diffraction pattern that introduces the rotational Doppler effect spatial modulation and diffracts the spatially shaped beam as shown in FIG. 1B. Lens L5 can be used to place the focal point of the beam 36 at the location of interest of the fluid flow 21 near a surface structure. In this regard, the system uses a fluid flow adjacent to the surface, as described above, in which the fluid has suspended micro particles. Should the fluid flow have a linear component, the particles go in-and-out of the region illuminated by the patterned beam at a certain speed that correlates with their linear velocity. If a particle moves linearly without rotating then the system will detect a signal rise and decay in a time T. The linear velocity would be the laser beam diameter at that position D divided by T. If a particle rotates and has a linear motion then the signal again would rise and decay in a time T, the linear velocity would be detected, as would oscillations at a frequency that is proportional to the angular velocity times the number of petals=2 the 'l' value.

The beam 36 is then focused with long focal length lens L3 and a first diffraction order is selected with an aperture. Lens L4 collimates the beam, which after reflection from the dichroic mirror (DM) 28, is focused by lens L5 (having focal length specified by the area being investigated) into the flow of moving fluid 21. The beam 36 diameter at the focus can be about 120 µm, an intensity that is at least one order of magnitude too weak for causing laser trapping or local heating.

Figure 15:
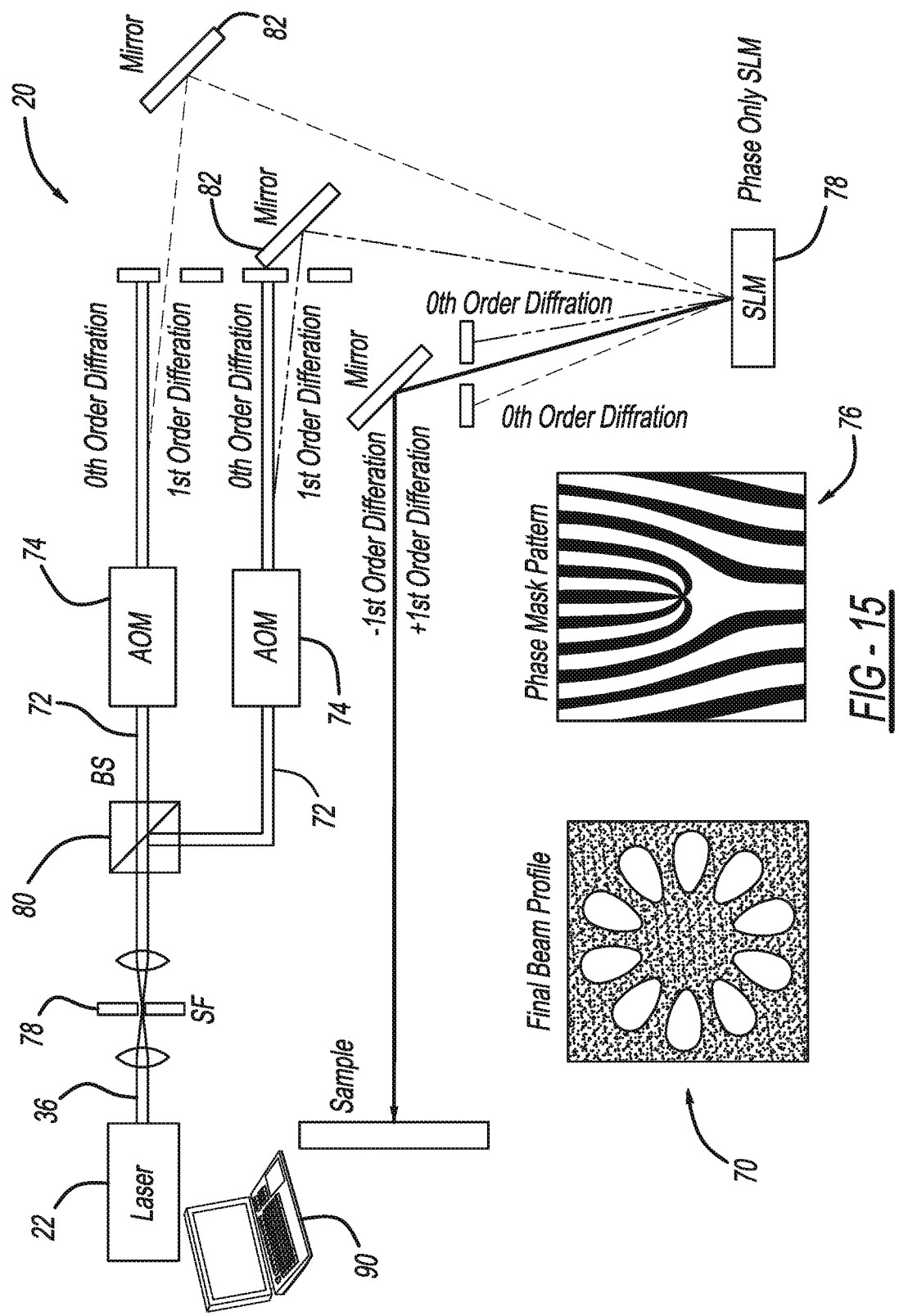
FIG. 15 is another configuration of a fluid measuring system.

Reference should now be made to another hardware configuration as shown in FIG. 15. This exemplary embodiment is used to generate a generally circular, spaced apart petal shaped beam pattern 30 by superposition of two Laguerre-Gaussian beams 72 with opposite signs of the same optical angular momentum. Utilizations of Acousto-Optical Modulator shapers (AOM) 74 can introduce a specified frequency difference between the two beams to produce a rotating final beam pattern. The phase mask 76 used on the phase-only Spatial Light Modulator (SLM) 78 and the ideal beam intensity profile generated using this method are also presented in the figure (for azimuthal index l=±5).

The laser beam 36 is cleaned up using a spatial filter (SF) system 78 and then it is split into two beams 72 with equal power using a beam splitter (BS) 80. Each of the split beams go through AOM 74 and their first order diffraction upon exit is collected and directed towards SLM 78 with the specified phase mask. Furthermore, mirrors 82 are used to align the beams in a manner so that the positive and negative first order diffractions of the reflected beams are collinear. The interference of these two beams generates the desired pattern 70. This is employed with lens L5 30, dichroic mirror DM 28, lens L6 30, aperture 38 and photodiode detector 34, as shown in FIG. 11.

In the FIG. 15 version, each arm produces a single LG profile (without petals). The interference of both arms at the sample causes the petals to appear, only where both beams overlap. This can also allow control of the depth where the measurement takes place. Furthermore, the AOM in each arm can introduce additional modulation that causes the petal pattern at the interference region to rotate. This beneficially allows one to determine the sign (rotation direction) of the vorticity being measured; and it allows one to make vorticity measurements that would be otherwise too slow or two fast. In other words, one can spin the petal at any arbitrary rate or direction. Using the setup in FIG. 15, one can make the measurements shown in FIGS. 12-14, where data is shown for different spinning rates (w in rpm) of the petal pattern.

Another way of describing this embodiment system is that it includes a laser beam split into two arms where at least one arm is modulated by an AOM. The two arms are then spatially modulated. The resulting beams interfere to form a spatial modulation that can be rotated arbitrarily by the first AOM. The spatial modulation in the beams is then used to measure fluid vorticity.

Figure 12:
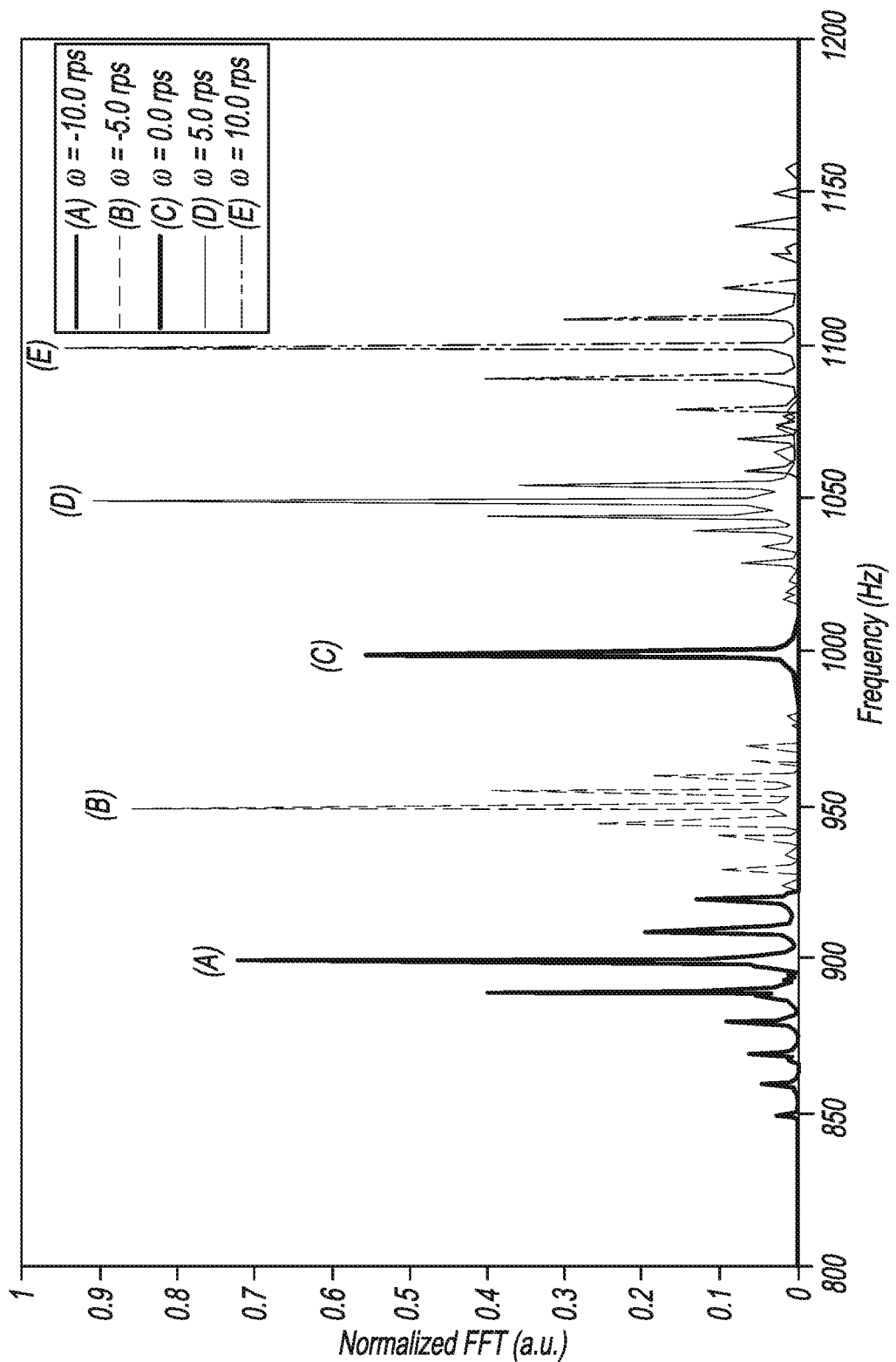
FIG. 12 represents measured signals from the system with a rotating sphere and a rotating beam pattern.

FIG. 12 illustrates sample power spectrum results from a rotating sphere with a rotating beam pattern. The plot shows normalized FFT of the acquired signal (y-axis) versus frequency (x-axis). Different line-styles (A-E) show results for cases with different sphere rotation speeds mentioned in legend. The beam pattern used for all cases is generated by superposing two Laguerre-Gaussian beams of the azimuthal index l=±5 (10 petals) and there is a 1000 Hz frequency difference between the two beams. Furthermore, it can be observed that there is a 1000 Hz bias in the frequency response of the system and rotational speeds of the same magnitude but different directions can now be distinguished by their shift relative to this frequency bias. The frequency observed in each case is $f_{observed}=f_{bias}+2l \times f_{rotation}$.

Figure 13B:
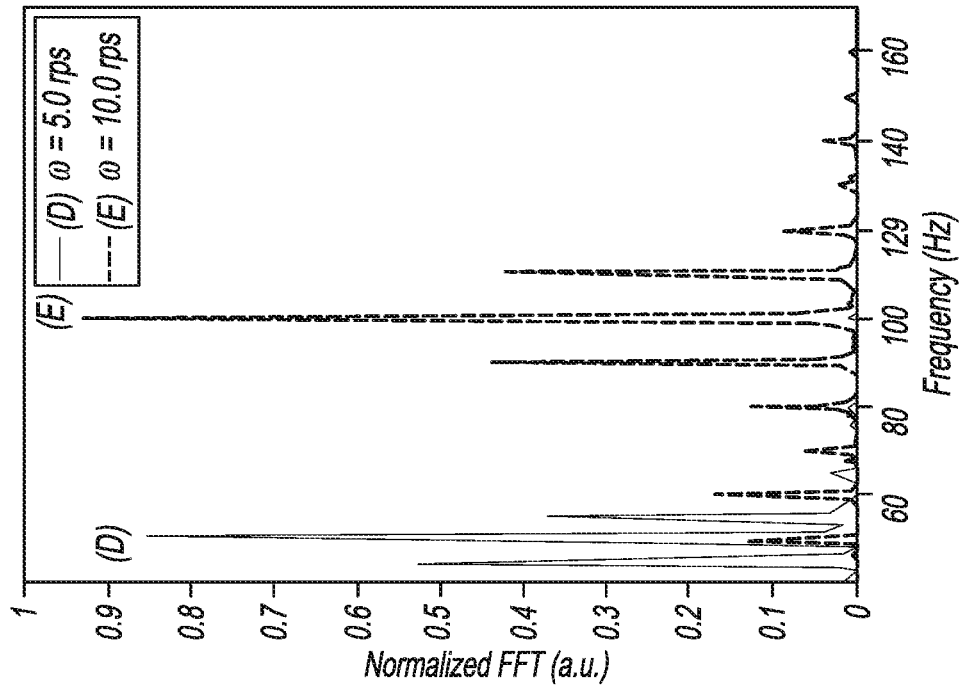
FIGS. 13A and 13B represent measured signals from the system with a rotating sphere and a stationary beam pattern.
Figure 13A:
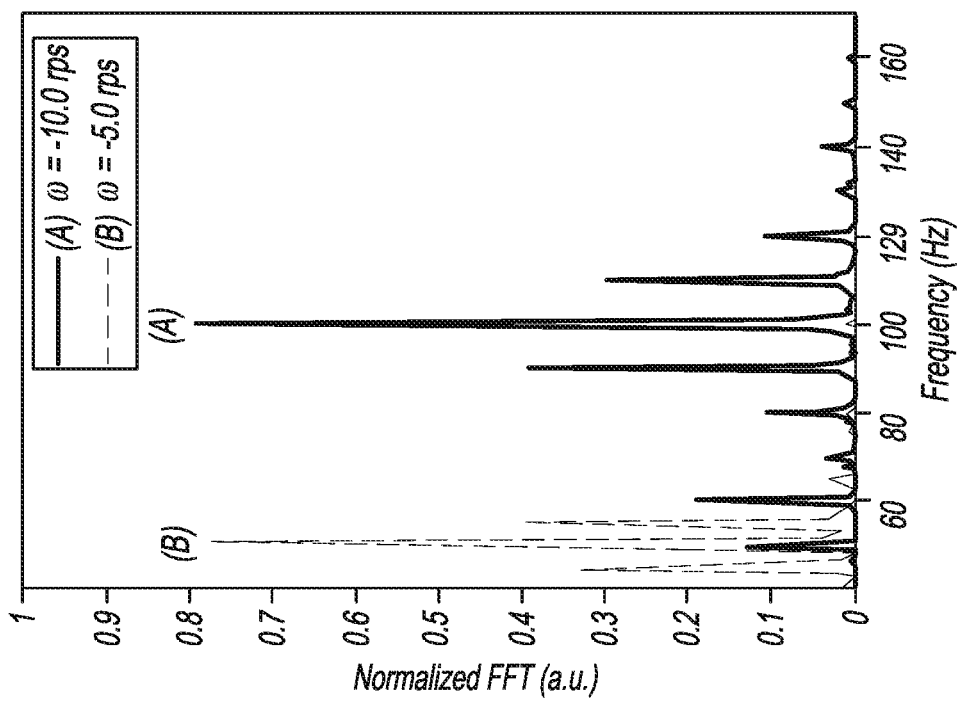

Referring to FIGS. 13A and 13B, sample power spectrum results are shown from a rotating sphere with a stationary beam pattern. Both plots show normalized FFT of the acquired signal (y-axis) versus frequency (x-axis). Different line styles (A-E) show results for cases with different sphere rotation speeds as mentioned in legends with a) showing negative and b) positive rotation speeds. Moreover, the stationary beam pattern used for all cases is generated by superposing two Laguerre-Gaussian beams of the azimuthal index l=±5 (10 petals) and there is no frequency difference between the two beams. It can be observed that rotational speeds of the same magnitude but different directions result in the same frequency response and therefore one cannot distinguish the direction of rotation. This exemplary system is blind to direction of rotation and only measures its magnitude. The frequency observed in each case is $f_{observed}=2l \times |f_{rotation}|$.

Figure 14:
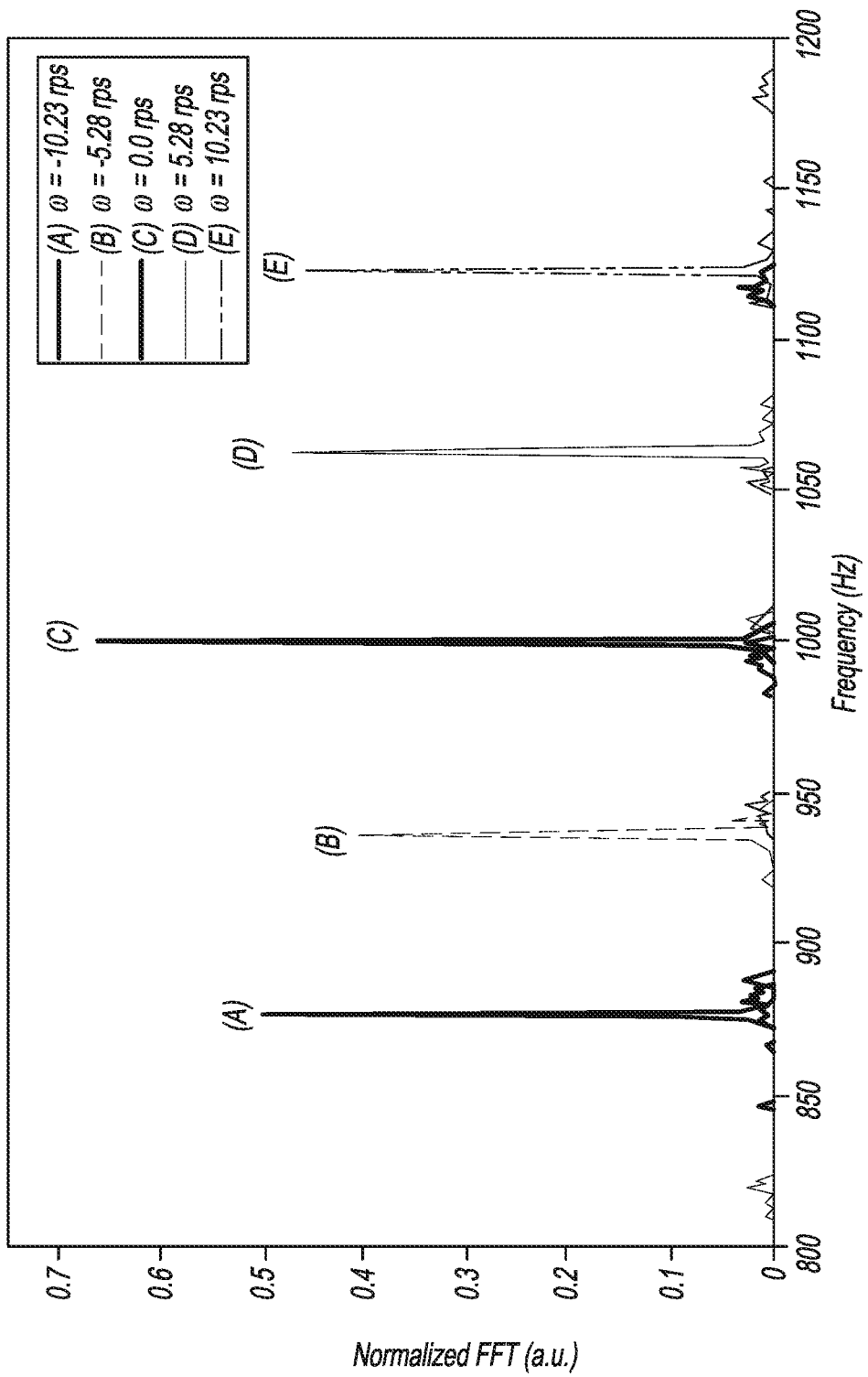
FIG. 14 represents measured signals from the system with a rotating disk and a rotating beam pattern.

Sample power spectrum results from a rotating disk with a rotating beam pattern can be observed in FIG. 14. The plot shows the normalized FFT of the acquired signal (y-axis) versus frequency (x-axis). Different line styles (A-E) show the results for cases with different disk rotation speeds mentioned in legend. The beam pattern used for all cases is generated by superposing two Laguerre-Gaussian beams of the azimuthal index l=±6 (12 petals) and there is a 1000 Hz frequency difference between the two beams. It can be observed that there is a 1000 Hz bias in the frequency response of the system and rotational speeds of the same magnitude but different directions can now be distinguished by their shift relative to this frequency bias. The frequency observed in each case is $f_{observed}=f_{bias}+2l \times f_{rotation}$.

It is also noteworthy for any of the embodiments discussed herein using scattering or fluorescing particles, the particles or scattering features may alternately be naturally present in the fluid. For example, such may include dust or bubbles which can alternately be seeded or artificially added to or created in the fluid as it is flowing in the container.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A system for direct and localized non-intrusive measuring of a vorticity in a fluid flow comprising:
    a laser configured to produce a Laguerre-Gaussian spatially modulated light beam that possess orbital angular momentum;
    an optic to focus the Laguerre-Gaussian beam at a location within a fluid flow, the fluid including particles;
    a photodiode configured receive a light signal from the particles and to produce a signal indicative of the light signal;
    a processor configured to do at least one of: (a) run an FFT on the signal indicative of the light signal to measure the vorticity of the fluid, or (b) to determine a frequency of the fluid from the scattered light signal.

2. The system of claim 1, wherein the Laguerre-Gaussian beam has a predetermined cross sectional pattern.

3. The system of claim 1, wherein the particles are of µm sized microparticles a reflection from which is detected by the photodiode for generating the indicating signal used by the processor to obtain an average fluid rotation rate about an optical axis of the light beam within a µm sized illumination region.

4. The system of claim 1, wherein the fluid comprises a plurality of the particles having a size between 2 µm and 150 µm.

5. The system of claim 4, wherein the particles are fluorescent polymer microspheres, further comprising a lens focusing epi-directional fluorescent light from the particles onto the photodiode.

6. The system of claim 1, wherein two Laguerre-Gaussian beams with opposing angular momentum are interfered at a distance where vorticity point measurements are desired, and a fixed amount of bias rotation frequency is added to both of the beams.

7. The system of claim 1, wherein the particles include a fluorescent microparticle.

8. The system of claim 1, further comprising:
a collimating lens acting on the light beam;
a component comprising at least one of: (a) an optical beam expander, or (b) an elongated optical fiber, located between the laser and the collimating lens;
a phase shaper located between the component and the fluid; and
the processor being a programmable computer connected to the photodiode, the computer determining vorticity of the fluid.

9. The system of claim 1, wherein the particles include bubbles.

10. The system of claim 1, further comprising multiple pulse shapers operably shaping split paths of the light beam.

11. A system for measuring vorticity in a fluid, the system comprising:
(a) a laser emitting a laser beam;
(b) a shaper shaping the emitted laser beam;
(c) an optic focusing the shaped laser beam at the fluid;
(d) at least one of the: (i) fluid and (ii) laser beam, rotating during an interaction between the shaped and focused laser beam and the fluid;
(e) a detector receiving reflected light from the laser beam and fluid interaction; and
(f) a computer measuring the vorticity of the fluid based on signals from the detector.

12. The system of claim 11, wherein the computer is adapted to directly determine magnitude and direction of the vorticity of the fluid in a noninvasive manner based on the signals from the detector.

13. The system of claim 11, wherein the detector includes a photodiode and the optic includes a lens.

14. The system of claim 11, wherein the shaper includes a phase-only SLM or AOM.

15. The system of claim 11, wherein the shaper includes a phase mask pattern comprising outwardly radiating and alternating contrasting stripes.

16. The system of claim 11, wherein the shaper includes a phase mask pattern comprising nested, elongated, curved and contrasting stripes.

17. The system of claim 11, wherein the shaper includes a phase mask pattern comprising intersecting straight stripes.

18. The system of claim 11, wherein the shaper includes a phase mask pattern comprising multiple dots against a contrasting background.

19. The system of claim 11, further comprising:
particles, each having a size between 2 and 150 µm, suspended in the fluid; and
the detector receiving the light reflected from the particles.

20. The system of claim 11, further comprising:
an AOM;
a beam splitter splitting the laser beam into multiple arms, at least one of the arms being modulated by the AOM;
spatially modulating the arms after the AOM modulation;
the AOM rotating the arms which interfere to form the spatial modulation; and
the spatial modulation in the arms being used for the measuring of the fluid vorticity.

21. A system for determining a flow of a fluid, the system comprising:
(a) a laser emitting a laser beam;
(b) a shaper including a phase mask pattern to shape the emitted laser beam, the phase mask pattern including multiple elongated stripes or spaced apart dots which contrast against a background area;
(c) a detector receiving reflected light from the laser beam interacting with the fluid; and
(d) a processor determining a characteristic associated with turbulence of the fluid based on an output from the detector.

22. The system of claim 21, further comprising bubbles in the fluid reflecting the light which is detected by the detector.

23. The system of claim 21, further comprising particles in the fluid which reflect the light, the particles each having a size between 2 µm and 150 µm.

24. The system of claim 21, further comprising a second shaper acting upon the laser beam.

25. The system of claim 21, wherein:
the processor is a programmable computer; and
the shaper is a phase-only SLM or AOM.

26. The system of claim 21, further comprising:
particles suspended in and rotating with the fluid; and
the processor being adapted to directly determine magnitude and direction of the turbulence of the fluid in a noninvasive manner based on the output from the detector which is based on reflected light from the particles.

27. The system of claim 21, wherein the stripes are used and outwardly radiate from a center point, and a final profile of the shaped laser beam includes multiple spaced apart petals arranged in a substantially circular pattern.

28. The system of claim 21, further comprising:
an AOM;
a beam splitter splitting the laser beam into multiple arms, at least one of the arms being modulated by the AOM;
spatially modulating the arms after the AOM modulation;
the AOM rotating the arms which interfere to form the spatial modulation; and
the spatial modulation in the arms being used for the determining of the fluid turbulence.

29. A system for measuring vorticity in a fluid, the system comprising:
(a) a laser emitting a laser beam;
(b) a shaper shaping the emitted laser beam;
(c) a detector receiving reflected light associated with the laser beam from the fluid;
(d) a computer measuring the vorticity of the fluid based on at least one signal from the detector;
(e) an AOM shaper;
(f) a beam splitter splitting the laser beam into multiple sub-beams, at least one of the sub-beams being modulated by the AOM shaper;
(g) spatially modulating the sub-beams after the AOM modulation;

(h) the AOM shaper rotating at least one of the sub-beams, such that the sub-beams interfere to create the spatial modulation;

(i) a second pulse shaper acting on a second of the sub-beams; and (j) the spatial modulation in the sub-beams assisting with the measuring of the fluid vorticity.

30. The system of claim 29, wherein the computer directly determines magnitude and direction of the vorticity of the fluid in a noninvasive manner based on the signal from the detector.

31. The system of claim 29, wherein the detector includes a photodiode.

32. The system of claim 29, further comprising:
particles, each having a size between 2 and 150 μm, suspended in the fluid; and
the detector receiving the light reflected from the particles.

33. The system of claim 29, wherein the shaper includes a phase mask pattern to shape the emitted laser beam, the phase mask pattern includes multiple elongated stripes or spaced apart dots which contrast against a background area.

34. The system of claim 29, wherein the AOM in each sub-beam introduces the modulation which causes a final beam profile and generally circular petal pattern at the interference to rotate.

35. The system of claim 29, wherein the fluid comprises a plurality of the particles each having a size between 2 μm and 150 μm.

36. The system of claim 35, wherein the particles are fluorescent polymer microspheres, further comprising a lens focusing epi-directional fluorescent light from the particles onto the photodiode.

37. The system of claim 29, further comprising bubbles in the fluid reflecting the light which is detected by the detector.

38. The system of claim 29, wherein the second pulse shaper is a phase only pulse shaper that is located optically downstream of the AOM shaper.

* * * * *